(12) United States Patent
Furuzono et al.

(10) Patent No.: US 8,515,524 B2
(45) Date of Patent: Aug. 20, 2013

(54) EXTRACORPERAL ULTRASONIC IRRADITION OF TITANIUM OXIDE (TIO2) COATED IMPLANT FOR ANGIOGENESIS STIMULATION

(75) Inventors: Tsutomu Furuzono, Suita (JP); Miwa Masuda, Suita (JP); Masahiro Okada, Suita (JP); Naotaka Nitta, Tsukuba (JP); Takashi Yamane, Tsukuba (JP)

(73) Assignees: National Cerebral and Cardiovascular Center, Osaka (JP); National Institute of Advanced Industrial Science and Technology, Tokyo (JP)

( * ) Notice: Subject to any disclaimer, the term of this patent is extended or adjusted under 35 U.S.C. 154(b) by 924 days.

(21) Appl. No.: 12/325,678

(22) Filed: Dec. 1, 2008

(65) Prior Publication Data

US 2009/0306552 A1 Dec. 10, 2009

(30) Foreign Application Priority Data

Jun. 4, 2008 (JP) ................................. 2008-147307
Nov. 21, 2008 (JP) ................................. 2008-298648

(51) Int. Cl.
*A61B 5/00* (2006.01)
(52) U.S. Cl.
USPC ................. 600/407; 600/437; 601/2; 601/46; 424/423
(58) Field of Classification Search
USPC .............. 73/504.01; 310/129, 313; 428/701; 435/173.8, 289.1; 524/497, 588; 600/347, 600/365, 437; 601/46; 604/118, 175; 623/1.49; 702/19
See application file for complete search history.

(56) References Cited

U.S. PATENT DOCUMENTS

| | | | |
|---|---|---|---|
| 5,921,933 A | 7/1999 | Sarkis et al. | |
| 6,355,006 B1 | 3/2002 | Ryaby et al. | |
| 6,432,070 B1 | 8/2002 | Talish et al. | |
| 6,547,951 B1 | 4/2003 | Maekawa | |

(Continued)

FOREIGN PATENT DOCUMENTS

| EP | 1 955 726 | 8/2008 |
|---|---|---|
| JP | 3-261467 A | 11/1991 |

(Continued)

OTHER PUBLICATIONS

Shimizu et al.; "Chô-onpa to nisankachitan wo mochiita yûgaibusshitsu no sakkin (Sterilization of hazardous microorganisms with use of ultrasonic waves and titanium dioxide)", Chô-onpa Riyôgijutsu Shûsei (Corpus of Ultrasonic Techniques), NTS, p. 115-125, 2005 (Partial translation provided).

(Continued)

*Primary Examiner* — Unsu Jung
*Assistant Examiner* — Serkan Akar
(74) *Attorney, Agent, or Firm* — Renner, Otto, Boisselle & Sklar, LLP

(57) ABSTRACT

The present invention solves the issue of bacterial infection by medical devices such as intracorporeal indwelling catheters. The present invention relates to an ultrasonic medical apparatus including a medical device (titanium oxide coated medical device 10) covered with a titanium oxide material (titanium oxide alone or a titanium oxide composite material) and ultrasonic irradiation means 20. Ultrasonic irradiation of the titanium oxide material, which exists on a surface of the medical device, causes the surface of the medical device to exert beneficial effects such as antibiotic action, the stimulation of angiogenesis, and the degradation of a blood clot and a biofilm.

14 Claims, 6 Drawing Sheets

(56) References Cited

U.S. PATENT DOCUMENTS

| | | | |
|---|---|---|---|
| 7,468,263 B2* | 12/2008 | Kishida et al. | 435/173.8 |
| 7,473,731 B2* | 1/2009 | Furuzono et al. | 524/588 |
| 7,611,782 B2* | 11/2009 | Furuzono et al. | 428/701 |
| 7,829,029 B2* | 11/2010 | Zumeris et al. | 422/127 |
| 2002/0188229 A1 | 12/2002 | Ryaby et al. | |
| 2003/0125679 A1 | 7/2003 | Kubota et al. | |
| 2003/0153848 A1 | 8/2003 | Talish et al. | |
| 2003/0153849 A1 | 8/2003 | Huckle et al. | |
| 2004/0230117 A1* | 11/2004 | Tosaya et al. | 600/439 |
| 2005/0119732 A1* | 6/2005 | Furuzono et al. | 623/1.49 |
| 2005/0153437 A1* | 7/2005 | Kishida et al. | 435/289.1 |
| 2005/0228111 A1* | 10/2005 | Furuzono et al. | 524/497 |
| 2005/0268921 A1 | 12/2005 | Zumeris et al. | |
| 2006/0052696 A1* | 3/2006 | Shiina et al. | 600/437 |
| 2006/0074314 A1 | 4/2006 | Slayton et al. | |
| 2006/0074355 A1 | 4/2006 | Slayton et al. | |
| 2006/0079816 A1 | 4/2006 | Barthe et al. | |
| 2007/0137300 A1* | 6/2007 | Dwyer et al. | 73/504.01 |
| 2007/0152538 A1* | 7/2007 | Huang et al. | 310/313 B |
| 2007/0200647 A1* | 8/2007 | Koyama et al. | 333/129 |
| 2007/0213645 A1* | 9/2007 | Zumeris et al. | 601/46 |
| 2008/0086042 A1* | 4/2008 | Brister et al. | 600/347 |
| 2008/0086044 A1* | 4/2008 | Brister et al. | 600/365 |
| 2008/0086273 A1* | 4/2008 | Shults et al. | 702/19 |
| 2008/0108942 A1* | 5/2008 | Brister et al. | 604/118 |
| 2008/0119703 A1* | 5/2008 | Brister et al. | 600/347 |
| 2008/0119704 A1* | 5/2008 | Brister et al. | 600/347 |
| 2008/0119706 A1* | 5/2008 | Brister et al. | 600/365 |
| 2008/0262349 A1 | 10/2008 | Kanehira et al. | |
| 2009/0216159 A1 | 8/2009 | Slayton et al. | |
| 2009/0306599 A1* | 12/2009 | Furuzono et al. | 604/175 |
| 2010/0318003 A1 | 12/2010 | Huckle et al. | |

FOREIGN PATENT DOCUMENTS

| | | |
|---|---|---|
| JP | 08-206193 | 8/1996 |
| JP | 2001-178825 A | 7/2001 |
| JP | 2002-522167 A | 7/2002 |
| JP | 2003-019177 | 1/2003 |
| JP | 2003-026406 | 1/2003 |
| JP | 2004-351331 | 12/2004 |
| JP | 2005-523132 A | 8/2005 |
| JP | 2005-288302 | 10/2005 |
| JP | 2007-275842 | 10/2007 |
| JP | 2008-500136 | 1/2008 |
| JP | 2008-030031 | 2/2008 |
| JP | 2008-94816 | 4/2008 |
| JP | 2008-514294 A | 5/2008 |
| JP | 2008-522642 A | 7/2008 |

OTHER PUBLICATIONS

H. Aoki, "Medical Applications of Hydroxyapatite" (Ishiyaku EuroAmerica, Inc., 1994), p. 133-155.

Okada et al., "Optimization of amino group density on surfaces of titanium dioxide nanoparticles covalently bonded to a silicone substrate for antibacterial and cell adhesion activities", J. Biomed, Mater. Res., 76A: 95-101, 2006.

Office Action for corresponding Japanese Application No. 2008-298648 mailed May 22, 2012.

Office Action for corresponding Japanese Application No. 2008-298648 mailed Feb. 12, 2013, with English translation.

* cited by examiner

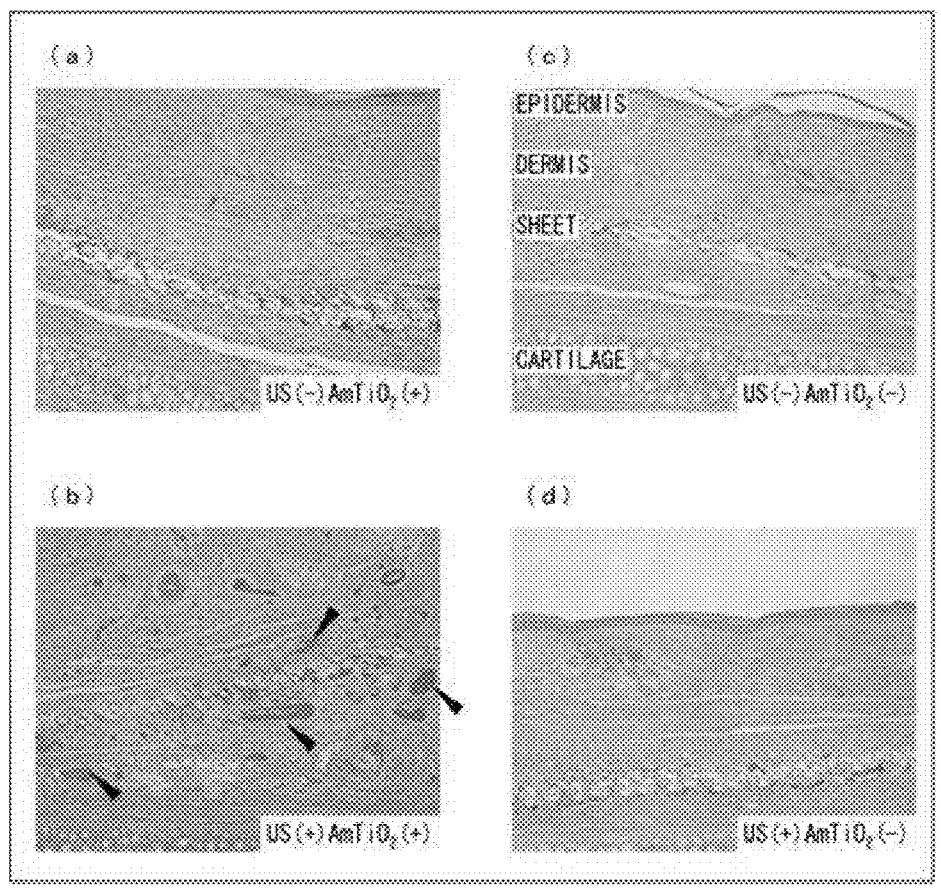

EXTRACORPERAL ULTRASONIC IRRADITION OF TITANIUM OXIDE (TIO2) COATED IMPLANT FOR ANGIOGENESIS STIMULATION

This Nonprovisional application claims priority under 35 U.S.C. §119(a) on Patent Application No. 147307/2008 filed in Japan on Jun. 4, 2008 and Patent Application No. 298648/2008 filed in Japan on Nov. 21, 2008, the entire contents of which are hereby incorporated by reference.

FIELD OF THE INVENTION

The present invention relates to an ultrasonic medical apparatus including a medical device covered with a titanium oxide material (titanium oxide alone or a titanium oxide composite material) and ultrasonic irradiation means. Ultrasonic irradiation of the titanium oxide material (titanium oxide alone or a titanium oxide composite material), which exists on a surface of the medical device, causes the surface of the medical device to exert beneficial effects such as antibiotic action, the stimulation of angiogenesis, and the degradation of a blood clot and a biofilm.

BACKGROUND OF THE INVENTION

It has been known that ultraviolet irradiation of titanium dioxide used as a photocatalyst causes the generation of highly oxidative hydroxy radicals (OH radicals), which has been used to eliminate organic substances such as organic compounds and bacteria. As a titanium dioxide excitation source other than ultraviolet rays, ultrasonic waves have drawn attention. It has been reported that low-frequency ultrasonic waves bring about the same bactericidal effect as ultraviolet rays do (see Non-patent Document 1).

This has been applied mainly in environmental fields, and such a technique has been known as to improve water quality and eliminate water microorganisms by irradiating titanium dioxide with ultrasonic waves. For example, for the purpose of providing a simply-structured sterilization apparatus and a sterilization method with significant effects of sterilizing fluids, Patent Document 1 discloses: a fluid sterilization apparatus including a flow channel along which fluids flow, an ultrasonic transducer, and an ultrasonic response diffuser; and a sterilization method. The technique of Patent Document 1 uses, as the ultrasonic response diffuser, a substance (e.g., titanium dioxide) that exhibits photocatalytic action when irradiated with ultrasonic waves, and sterilizes the fluids by irradiating the ultrasonic response diffuser with ultrasonic waves.

Further, the bactericidal effect of ultrasonic irradiation of titanium dioxide has been confirmed by the fact that the concentration of *Escherichia coli* decreased when titanium dioxide was excited by ultrasonic waves with an output of 200 W at a frequency of 39 kHz (see Non-patent Document 1).

Further, Patent Document 2 discloses a method for producing hydroxy radicals through ultrasonic irradiation of water containing titanium dioxide particles.

Further, for the purpose of degrading organic constituents or, in particular, persistent hazardous organic compounds present in the water and detoxifying pathogenic microorganisms present in the water, Patent Document 3 discloses: a water treatment method for, during ultrasonic irradiation of water in which titanium dioxide exists, adding an antioxidant such as hydrogen peroxide into the water being treated; and an apparatus that is used for the method.

Further, for the purpose of providing a method for treating an organic substance, Patent Document 4 discloses a method for irradiating an organic substance with ultrasonic waves in the presence of an organic-substance treating agent. Examples of the organic substance encompass fungi, bacteria, and viruses, and examples of the organic-substance treating agent encompass titanium oxide deficient in oxygen.

Further, Patent Document 5 discloses a liquid treatment method characterized in that a liquid, containing organic matter, which is to be treated is irradiated with ultrasonic waves in the presence of titanium oxide composite woody carbide and hydrogen peroxide and the organic matter is thereby degraded.

In addition to the foregoing techniques, examples of techniques that involve the use of ultrasonic waves and titanium oxide encompass the following techniques. For example, Patent Document 6 discloses a method and apparatus for treating organic-pollutant-containing waste water through oxidative degradation of organic pollutants in a radical reaction by hydroxy radicals. The hydroxy radicals here are electrically generated by using titanium dioxide as a positive electrode. Further, ultrasonic waves are used to overcome such a disadvantage that a considerable amount of energy is used to charge suspended particles contained, if any, in waste water being treated and such a disadvantage that a radical-generating reaction is significantly slowed down due to deposition of a large number of particles in a hole of a metal oxide electrode.

Further, Patent Document 7 discloses a cosmetic tool that concurrently generates ultrasonic waves and far-infrared rays by passage through a titanium oxide head or a metal plate. Although Patent Document 7 gives no examples and therefore lacks clarity about principles or mechanisms, Patent Document 7 says that the ultrasonic output is activated by passage through the titanium oxide plate and the promotion of a massaging effect is thereby achieved.

Incidentally, there has been an issue of bacterial infection due to contamination of skin openings by medical devices such as intracorporeal indwelling catheters, gastrostomy catheters, and tracheostomy tubes. When implanted in a living organism, an intracorporeal indwelling catheter or the like is recognized as a foreign object by the living organism's tissue. Moreover, the living organism's tissue and the medical device do not make close contact with each other. Therefore, for example, in the case of a percutaneous catheter, the epidermis is pushed inward along the catheter, i.e., there occurs epithelial downgrowth (which is a phenomenon that causes the epithelial tissue to invaginate along a surface of the catheter). Moreover, deepening of the epithelial downgrowth renders sterilization incomplete and causes the formation of a route of bacterial infection, thus causing inflammation of the skin. Eventually, there is no alternative but to dislodge the intracorporeal indwelling catheter. In order to solve such a problem, there has been proposed various intracorporeal indwelling medical devices designed to make close contact with living organisms.

For example, an intracorporeal indwelling catheter such as an interperitoneal indwelling catheter or a central venous catheter includes a cuff member (Dacron cuff), made of Dacron unwoven cloth, which serves to prevent bacterial infection and fix the catheter in a living organism (e.g., see Patent Document 8). Subcutaneous implantation of the Dacron cuff leads to proliferation of subcutaneous connective tissue, with the result that the catheter is fixed so firmly as to be less likely to be dislodged by accident. However, even in the case of such a catheter, the Dacron cuff does not make close contact with the living organism's tissue, and therefore cannot completely prevent bacterial infection.

Further proposed as an intracorporeal indwelling medical device is a percutaneous terminal made of a highly biocompatible hydroxyapatite ceramic (see Non-patent Document 2). According to the arrangement of Non-patent Document 2, the percutaneous terminal is constituted solely by a hydroxyapatite ceramic. Hyrdorxyapatite is a component of a tooth and exhibits an excellent affinity for soft tissue. However, hydroxyapatite is hard and fragile. Therefore, the percutaneous terminal is hard and, when implanted in a living organism, may leave space between the hydroxyapatite ceramic and the living organism's tissue. That is, the percutaneous terminal makes poor contact with the living organism. Furthermore, manufacture of a percutaneous terminal solely from a hydroxyapatite ceramic causes an undesirable increase in size of the percutaneous terminal. As such, the arrangement of Non-patent Document 2 is riddled with various problems. For example, the percutaneous terminal is fragile. Further, when implanted in a living organism, the percutaneous terminal brings discomfort to the patient because of its hardness.

[Patent Document 1]
Japanese Unexamined Patent Application Publication No. 275842/2007 (Tokukai 2007-275842; published on Oct. 25, 2007)
[Patent Document 2]
Japanese Unexamined Patent Application Publication No. 26406/2003 (Tokukai 2003-26406; published on Jan. 29, 2003)
[Patent Document 3]
Japanese Unexamined Patent Application Publication No. 351331/2004 (Tokukai 2004-351331; published on Dec. 16, 2004)
[Patent Document 4]
Japanese Unexamined Patent Application Publication No. 30031/2008 (Tokukai 2008-30031; published on Feb. 14, 2008)
[Patent Document 5]
Japanese Unexamined Patent Application Publication No. 288302/2005 (Tokukai 2005-288302; published on Oct. 20, 2005)
[Patent Document 6]
Japanese Translation of PCT Patent Application Publication No. 538960/2002 (Tokuhyo 2002-538960; published on Nov. 19, 2002)
[Patent Document 7]
Japanese Unexamined Patent Application Publication No. 19177/2003 (Tokukai 2003-19177; published on Jan. 21, 2003)
[Patent Document 8]
Japanese Unexamined Patent Application Publication No. 206193/1996 (Tokukaihei 8-206193; published on Aug. 13, 1996)
[Non-patent Document 1]
Shimizu, N., Ogino, C., and Dadjour, M. F.: "Chô-onpa to nisankachitan wo mochiita yûgaibusshitsu no sakkin (Sterilization of hazardous microorganisms with use of ultrasonic waves and titanium dioxide)", *Chô-onpa Riyôgijutsu Shûsei (Corpus of Ultrasonic Techniques)*, NTS, p. 115-125, 2005.
[Non-patent Document 2]
Aoki, H.: "Medical Applications of Hydroxyapatite", (Ishiyaku EuroAmerica, Inc., 1994), p. 133-155.

SUMMARY OF THE INVENTION

As mentioned above, there has been an issue of bacterial infection due to contamination of skin openings by medical devices such as intracorporeal indwelling catheters, gastrostomy catheters, and tracheostomy tubes. However, no means for solving this issue has been found yet. The present invention has been made in order to solve the foregoing problems.

The inventors have diligently studied to solve the foregoing problems. In the result, the inventors have found that the foregoing problems can be solved by applying the bactericidal effect of ultrasonic excitation of titanium oxide to a medical device. Thus, the inventors have completed the present invention.

That is, in order to solve the foregoing problems, an ultrasonic medical apparatus according to the present invention includes: a medical device whose surface has been covered with a titanium oxide material; and ultrasonic irradiation means for irradiating the medical device with ultrasonic waves, the titanium oxide material being a material composed solely of titanium oxide or a titanium oxide composite material produced by covering a surface of a polymer base material with titanium oxide.

In the ultrasonic medical apparatus according to the present invention, the ultrasonic irradiation means may be means capable of radiating ultrasonic waves with an output falling within safety standards for living organisms.

In the ultrasonic medical apparatus according to the present invention, the ultrasonic irradiation means may be adjustable for output of ultrasonic waves.

In the ultrasonic medical apparatus according to the present invention, the ultrasonic irradiation means may be means capable of generating one or more types of ultrasonic waves selected from the group consisting of continuous waves, pulse waves, burst waves, and standing waves.

In the ultrasonic medical apparatus according to the present invention, the ultrasonic irradiation means may be means capable of radiating focused ultrasonic waves.

In the ultrasonic medical apparatus according to the present invention, the ultrasonic irradiation means may include a coupler.

In the ultrasonic medical apparatus according to the present invention, the ultrasonic irradiation means may be constituted by a transducer composed of a piezoelectric substance having a coefficient of electromechanical coupling of not less than 10%.

In the ultrasonic medical apparatus according to the present invention, the transducer, which constitutes the ultrasonic irradiation means, may be composed of a piezoelectric substance that is a quartz crystal, a water-soluble crystal, a piezoceramic, a polymer piezoelectric material, a highly-bound piezoelectric material, an electrodeposited piezoelectric material, a composite piezoelectric material, or any combination of the materials.

In the ultrasonic medical apparatus according to the present invention, the ultrasonic irradiation means may be means capable of generating ultrasonic waves at a frequency of not less than 150 kHz.

In the ultrasonic medical apparatus according to the present invention, the ultrasonic irradiation means may be means capable of generating, in a single transmission, ultrasonic waves containing higher harmonic waves or multi-frequency waves.

In the ultrasonic medical apparatus according to the present invention, the titanium oxide composite material may be composed of (a) a polymer base material having an active group and (b) titanium oxide having a reactive functional group capable of reacting with the active group and be produced through chemical bonding between the active group and the reactive functional group.

In the ultrasonic medical apparatus according to the present invention, the titanium oxide composite material may be composed of (a) a polymer base material having an active group and (b) titanium oxide having an amino group and be produced through chemical bonding between the active group and the amino group.

In the ultrasonic medical apparatus according to the present invention, the titanium oxide composite material may be produced through a hydroxyl group possessed by titanium oxide and a functional group, possessed by a polymer base material, which is capable of forming a chemical bond with the hydroxyl group.

In the ultrasonic medical apparatus according to the present invention, the titanium oxide composite material may satisfy either or both of the following conditions (i) and (ii): (i) the titanium oxide composite material is composed of (a) a polymer base material having an active group and (b) titanium oxide having an amino group and is produced through chemical bonding between the active group and the amino group; and (ii) the titanium oxide composite material is produced through a hydroxyl group possessed by titanium oxide and a functional group, possessed by a polymer base material, which is capable of forming a chemical bond with the hydroxyl group.

In the ultrasonic medical apparatus according to the present invention, the medical device may be a medical device whose surface has been covered with the titanium oxide material by flocking.

In the ultrasonic medical apparatus according to the present invention, the medical device may be an implantable medical device, an extracorporeal-intracorporeal medical device, or a body surface contact medical device.

As mentioned above, the bactericidal technique that involves the ultrasonic irradiation of titanium oxide has been applied mainly in environmental fields as a technique for improving water quality and eliminating water microorganisms. It has been neither disclosed nor suggested that such a technique is applied in the field of medical devices.

An ultrasonic medical apparatus according to the present invention is obtained through a combination of: a medical device whose surface has been covered with a titanium oxide material (a material composed solely of titanium oxide or a titanium oxide composite material produced by covering a surface of a polymer base material with titanium oxide); and ultrasonic irradiation means for irradiating the medical device with ultrasonic waves. Ultrasonic irradiation of the titanium oxide, which exists on the surface of the medical device, causes the titanium oxide to be excited to generate OH radicals. This makes it possible to cause the surface of the medical device to exert bactericidal action and antibacterial action. This makes it possible to solve the issue of bacterial infection by medical devices such as intracorporeal indwelling catheters, gastrostomy catheters, and tracheostomy tubes (anti-infective effect).

Even more surprisingly, the ultrasonic medical apparatus according to the present invention brings about a remarkable and advantageous effect of stimulating angiogenesis induced by cytokines (e.g., TNFα) secreted from tissue surrounding the medical device irradiated with ultrasonic waves. Such an effect cannot be anticipated even by a person skilled in the art. The stimulation of angiogenesis brings about a tissue-healing effect and an anti-infective effect. Further, the technique of the present invention is expected to be effective also in regenerative medicine. The inventors believe that the stimulation of angiogenesis is achieved by angiogenesis stimulators, such as cytokines TNFα, produced when the tissue surrounding the medical device is stimulated by OH radicals or superoxide radicals generated by the ultrasonic irradiation of the titanium oxide. It should be noted that the angiogenesis stimulators that are secreted may be publicly-known angiogenesis stimulators such as VEGF, TVPF, PD-ECGF, ESAF, Angiotropin, Angiogenin, FGF, IL-8, IGF-1, TGF-α, TGF-β, PDGF, HGF, GCSF, Proliferin, Substance P, and ProstagIndin.

Further, the ultrasonic medical apparatus according to the present invention brings about a remarkable and advantageous effect of stimulating the degradation of a blood clot and a biofilm on the surface of the medical device irradiated with ultrasonic waves. Such an effect cannot be anticipated even by a person skilled in the art. The degradation of a blood clot and a biofilm makes it possible to enhance the anti-infective effect. The biofilm is a cause of catheter infection. In cases where there is an infection focus in a distant site, the bacteria are carried by the bloodstream, are firmly fixed onto the surface of a catheter placed in a blood vessel, and form a biofilm (see Takano, Y.: "Katêteru Kansen (Catheter Infection)", *Nichii Zasshi* (*Journal of the Japan Medical Association*), Vol. 127, No. 3, p. 381-384, 2002). Further, a blood clot adhering to the surface of a catheter is likely to provide a foothold for fixation of bacteria, and can therefore cause the formation of a biofilm. The degradation of a blood clot and a biofilm in a catheter site placed in a blood vessel and exposed to blood eliminates a foothold for proliferation of bacteria, thus enhancing the anti-infective effect. Further, the application of the technique of the present invention to stents or the like makes it possible to prevent vascular obstruction. It should be noted that the inventors believe that the degradation of a blood clot and a biofilm is achieved by OH radicals' stimulating the degradation of clot-forming protein, such as fibrin, that makes up a blood clot and the degradation of bacteria that form a biofilm or of extracellular polysaccharides secreted by bacteria.

Additional objects, features, and strengths of the present invention will be made clear by the description below. Further, the advantages of the present invention will be evident from the following explanation in reference to the drawings.

BRIEF DESCRIPTION OF THE DRAWINGS

FIG. 7 shows photographs (a) to (d) of specimens subjected to HE staining in Example 4, the photograph (a) being a photograph of a specimen obtained by using a titanium oxide complex sheet and without ultrasonic irradiation (US(−)AmTiO$_2$(+)), the photograph (b) being a photograph (US(+)AmTiO$_2$(+)) of a specimen obtained by using a titanium oxide complex sheet and with ultrasonic irradiation, the photograph (c) being a photograph of a specimen obtained by using an untreated polyester (PET) sheet and without ultrasonic irradiation (US(−)AmTiO$_2$(−)), the photograph (d) being a photograph of a specimen obtained by using an untreated polyester (PET) sheet and with ultrasonic irradiation (US(+)AmTiO$_2$(−)).

DESCRIPTION OF THE EMBODIMENTS

Figure 1:
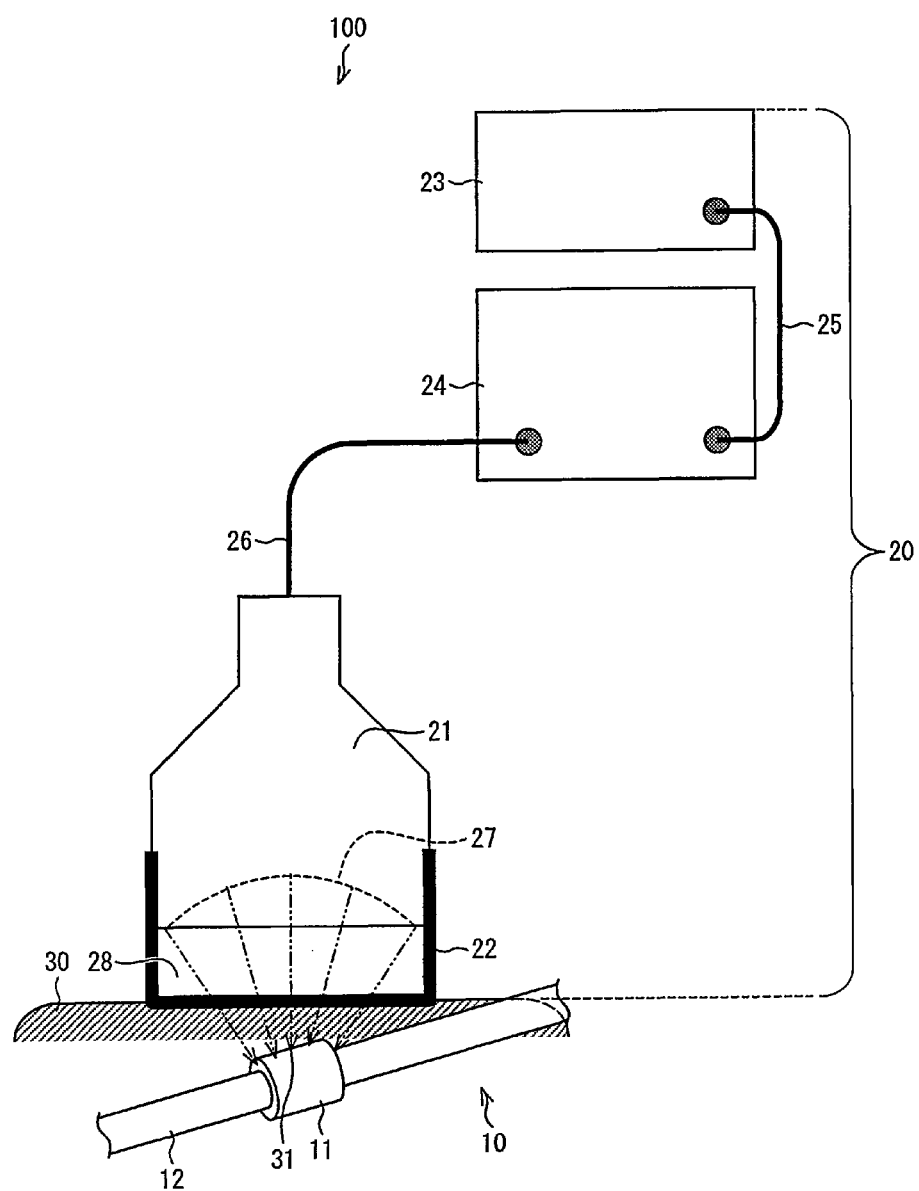
FIG. 1 schematically shows an arrangement of an ultrasonic medical apparatus according to an embodiment of the present invention.

An embodiment of the present invention will be described below. It should be noted that the present invention is not limited to this. It should also be noted that all the non-patent and patent documents listed in this specification are used also as references in this specification.

An ultrasonic medical apparatus of the present invention includes: (1) a medical device whose surface has been covered with a titanium oxide material (such a medical device being hereinafter referred to as "titanium oxide coated medical device"); and (2) ultrasonic irradiation means for irradiating the medical device with ultrasonic waves.

<1. Titanium Oxide Coated Medical Device>

The "titanium oxide coated medical device", which constitutes the ultrasonic medical apparatus of the present invention, is a medical device whose surface has been covered with a titanium oxide material.

(1-1. Titanium Oxide Material)

The term "titanium oxide material" here means a material composed solely of titanium oxide (i.e., titanium oxide) or a titanium oxide composite material produced by covering a surface of a polymer base material with titanium oxide. It should be noted here that the titanium oxide is not particularly limited, and it is possible to use titanium oxide listed in *Iwanami Rikagaku Jiten* (*Iwanami Dictionary of Physics and Chemistry*), Fourth Edition (Iwanami Shoten, Publishers). For example, titanium dioxide represented by the chemical formula (TiO$_2$) can be used in the present invention. It should be noted that the titanium oxide TiO$_2$ has a hydroxyl group on a surface thereof. Specifically, in the case of TiO$_2$, there exist two types of hydroxyl group on crystal faces occupying most of the surface of titanium oxide, i.e., on an anatase-type face (001) and a rutile-type face (110). One is a terminal OH group binding to one Ti$^{4+}$, and the other is a bridge OH group binding to two Ti$^{4+}$'s (see Seino, M.: *Sanka Chitan: Bussei to Ôyô Gijutsu* (*Titanium Oxide: Physical Properties and Applied Technology*), Gihodo Shuppan Co., Ltd., 2000).

Further, the titanium oxide for use in the present invention is not particularly limited in form. However, in order to cover the surface of the medical device or of the polymer base material, it is more preferable that the titanium oxide be in the form of particles. In the form of particles, the titanium oxide particles only needs to have such a particle shape and a particle diameter that the titanium oxide can cover the surface of the medical device or of the polymer base material. Specifically, it is preferable that the particle diameter be at least not less than 0.001 μm, or more preferably not less than 0.01 μm. On the other hand, it is preferable that the particle diameter be at most not more than 1000 μm, or more preferably not more than 100 μm.

There is no particular limit on how to cover the surface of the medical device with the material composed solely of titanium oxide (i.e., titanium oxide), how to obtain the titanium oxide composite material by covering the surface of the polymer base material with the titanium oxide, or how to cover the surface of the medical device with the titanium oxide composite material. However, for example, it is possible to apply a method, such as dipping, spin coating, spraying, or screen printing, for physically adsorbing the titanium oxide or the titanium oxide composite material into the surface of the medical device or of the polymer base material. It is also possible to use an adhesive or the like in physically adsorbing the titanium oxide or the titanium oxide composite material into the surface of the medical device or of the polymer base material. For the above methods, refer to (1) "Hashimoto, K. and Fujishima, A. ed.: *Zukai Hikarishokubai no Subete* (*All about Photocatalysts Illustrated*), Kogyo Chosakai Publishing, Inc., p. 176-203 (2003)", (2) "Fujishima, A., Hashimoto, K., and Watanabe, T.: *Hikarishokubai no Shikumi* (*Mechanisms of Photocatalysts*), Nippon Jitsugyo Publishing Co., Ltd., p. 142-143 (2001)", and (3) "Nosaka, Y. and Nosaka, A.: *Nyumon Hikarishokubai* (*Introduction to Photocatalysts*), Tokyo Tosho Co., Ltd., p. 145-172 (2004)", for example.

It is also possible to cover the surface of the polymer base material with the titanium oxide by chemical bonding, because the titanium oxide can be adsorbed firmly and stably into the surface of the polymer base material. Examples of such an aspect obtained by covering a surface of a polymer base material with titanium oxide with use of a chemical bond encompass an aspect composed of (a) a polymer base material having an active group and (b) titanium oxide having a reactive functional group (e.g., an amino group) capable of reacting with the active group and produced through chemical bonding between the active group and the reactive functional group (Aspect (i)). Another possible example is an aspect produced, as described above, through chemical bonding between a hydroxyl group on the surface of titanium oxide (TiO$_2$) and a functional group, possessed by a polymer base material, which is capable of forming a chemical bond with the hydroxyl group (Aspect (ii)). An embodiment of the present invention only needs to cover a surface of a polymer base material with titanium oxide via a chemical bond in either or both of Aspect (i) and Aspect (ii).

For such a method for covering a surface of a polymer base material with titanium oxide via a chemical bond, refer to International Publication No. 2005/019317 Pamphlet (published on Mar. 3, 2005) and "Okada, M., Yasuda, S., Kimura, T., Iwasaki, M., Ito, S., Kishida, A., and Furuzono, T.: *J. Biomed. Mater. Res.*, 76A: 95-101, 2006". See below for more details.

It is preferable that the polymer base material for use in the present invention be a medical polymer base material, or more preferably an organic polymer. Specific examples of the polymer base material encompass: synthetic polymers such as a silicone polymer (or silicone rubber), polyethylene glycol, polyalkylene glycol, polyglycolic acid, polylactic acid, polyamide, polyurethane, polysulfone, polyether, polyether ketone, polyamine, polyurea, polyimide, polyester, polyethylene, polypropylene, polytetrafluoroethylene, polyacrylic acid, polymethacrylic acid, methyl polymethacrylate, polyacrylonitrile, polystyrene, polyvinyl alcohol, and polyvinyl chloride; polysaccharides such as cellulose, amylose, amylopectin, chitin, and chitosan; polypeptides such as collagen; mucopolysaccharides such as hyaluronic acid, chondroitin, and chondroitin sulfate; natural polymers such as silk fibroin. Among the polymer base materials thus taken as examples, a silicone polymer, polyurethane, polytetrafluoroethylene, or silk fibroin is suitably used because of excellence in properties such as long-term stability, strength, and flexibility. Further, the polymer base materials may be in the form of a sheet, a fiber, a tube, or a porous body, any one of which may be selected appropriately according to the intended purpose.

The following describes a method for covering a surface of a polymer base material with titanium oxide via a chemical bond (esp., a method for forming Aspect (i)). This method is a method for producing a titanium oxide composite material through chemical bonding between titanium oxide and a polymer base material, the method including: an active group introducing step of introducing an active group into the polymer base material; a reactive functional group introducing step of introducing, into the titanium oxide, a reactive functional group capable of reacting with the active group; and a reacting step of causing a reaction between the active group and the reactive functional group.

More specifically, for example, such an example is described where: silicone rubber obtained through graft polymerization of a vinyl-based polymerizable monomer having a carboxyl group on a surface thereof is used as a polymer base material having an active group; titanium oxide having an amino group introduced thereinto is used as particles of titanium oxide having a reactive functional group introduced to a surface thereof; and the titanium oxide covers a surface of the polymer base material via a chemical bond through a reaction between the titanium oxide and the polymer base material. According to this method, the chemical bond between the titanium oxide and the polymer base material is formed through a reaction between the active group and the reactive functional group.

The chemical bond between the titanium oxide and the polymer base material is not particularly limited, provided the strength of bonding between the titanium oxide and the polymer base material is sufficient. For example, such a case is specifically described where the chemical bond between the titanium oxide and the polymer base material is an amide bond. An amide bond is obtained, for example, through (a) a reaction between an amino group and a carboxyl group, an azidocarbonyl group, a chlorocarbonyl group, N-hydroxysuccinimide carboxylic acid ester, or acid anhydride, (b) a reaction between a carboxyl group and an N-acetylamino group or an N-trimethylsilylamino group, or (c) a reaction between an isocyanate group and a carboxylic group. Different combinations require different reaction conditions. There is no particular limit on reaction conditions, provided a reaction proceeds.

For example, in the case of a combination of an amino group and a carboxylic group, the titanium oxide is added, stirred, and dispersed into a solvent first. After that, the polymer base material is immersed in the solvent. Then, the polymer base material is washed after being withdrawn from the solvent, and the active group of the polymer base material and the reactive functional group of the titanium oxide are brought into reaction (condensation reaction) under specific reaction conditions. At this time, it is preferable that the titanium oxide be used at least in an amount of not less than 0.001 parts by weight, or more preferably not less than 0.01 parts by weight, with respect to 1 part by weight of the polymer base material having the active group. On the other hand, it is preferable that the titanium oxide be used at most in an amount of not more than 100 parts by weight, or more preferably not more than 50 parts by weight, with respect to 1 part by weight of the polymer base material having the active group. Further, specific examples of the solvent in which the titanium oxide is dispersed encompass: water; hydrocarbon solvents such as toluene and hexane; alcohols; ether solvents such as tetrahydrofuran and diethylether; and ketone solvents such as acetone and methyl ethyl ketone. It is preferable that the solvent be used at least in an amount of not less than 0.1 parts by weight, or more preferably not more 1.0 part by weight, with respect to 1 part by weight of the polymer base material. On the other hand, it is preferable that the solvent be used at most in an amount of not more than 1000 parts by weight, or more preferably not more than 500 parts by weight, with respect to 1 part by weight of the polymer base material.

Moreover, it is preferable that the reaction temperature at which the active group of the polymer base material and the reactive functional group of the titanium oxide are brought into reaction after the withdrawal of the polymer base material from the solvent be at least not less than 120° C., more preferably not less than 140° C., or still more preferably not less than 160° C. On the other hand, it is preferable that the reaction temperature be at most not more than 200° C., or more preferably not more than 180° C.

Further, it is preferable that the condensation reaction be performed under reduced pressure. It is preferable that the degree of reduced pressure be at least not less than 0.01 mmHg (1.33 Pa), or more preferably not less than 0.1 mmHg (13.3 Pa). On the other hand, it is preferable that the degree of reduced pressure be at most not more than 10 mmHg (1.33 kPa), or more preferably not more than 5.0 mmHg (0.665 kPa). Further, in the case of formation of an amide bond by an amino group and a carboxylic group, a synthesis can be achieved at a low temperature by using a condensing agent such as carbodiimide. Specifically, the amide bond can be formed by continuing with a reaction for 1 to 6 hours at a temperature of 4° C. to room temperature (25° C.).

The following describes the step (active group introducing step) of introducing an active group into the polymer base material. Examples of a method for introducing an active group into the polymer base material encompass a method for introduction by a surface graft polymerization method after giving acid/alkali treatment, corona discharge, and/or plasma irradiation to a surface of the polymer base material. It should be noted that the active group may be an active group inherent in a polymer on the surface of the polymer base material.

Described here is an example of a method for introducing an active group into polydimethylcyclohexane-based silicone rubber as a polymer base material with use of the surface graft polymerization method. In the case of introduction of an active group into polydimethylsiloxane-based silicone rubber as a polymer base material by graft polymerization, a surface of the polymer base material is subjected to corona treatment or plasma irradiation first. After that, the polymer base material thus treated and a polymerizable monomer having the active group are poured into a solvent and then polymerized in an atmosphere of inert gas and under reduced pressure.

Examples of the solvent encompass: water; hydrocarbon solvents such as toluene and hexane; alcohols; ether solvents such as tetrahydrofuran and diethylether; and ketone solvents such as acetone and methyl ethyl ketone. It is preferable that the solvent be used at least in an amount of not less than 0.1 parts by weight, or more preferably not more 1.0 part by weight, with respect to 1 part by weight of the polymer base material thus treated. On the other hand, it is preferable that the solvent be at most in an amount of not more than 1000 parts by weight, or more preferably not more than 500 parts by weight, with respect to 1 part by weight of the polymer base material thus treated.

Further, there is no particular limit on the polymerizable monomer for use in the graft polymerization, provided the polymerizable monomer has, at a terminal (or side chain) thereof, an active group that forms a chemical bond in reaction to a reactive functional group on the surface of titanium oxide particles. Specific examples of the polymerizable monomer encompass: (meth)acrylic acid, aconitic acid, itaconic acid, mesaconic acid, citraconic acid, fumaric acid, maleic acid, vinylsulfonic acid, acrylamide-2-methylpropanesulfonic acid, vinylsulfonic acid, and various metal salts or haloids thereof; (meth)acrylamide, 2-hydroxyethyl(meth) acrylate, (meth)acrylic acid monoglycerol, N-[tris(hydroxymethyl)methyl]acrylamide, N-vinyl pyrrolidone, N-(meth)acryloyl pyrrolidone, acryloyl morpholine, imide maleate, and anhydrous maleic acid; styrene-based monomers such as aminostyrene and carboxystyrene; and glycidyl (meth)acrylate, (meth)acryloyloxyethyltrimethoxysilane, and vinylbenzylamine.

It is preferable that the polymerizable monomer be added at least in an amount of not less than 0.001 parts by weight, or more preferably not less than 0.01 parts by weight, with respect to 1 part by weight of the titanium oxide particles. On the other hand, it is preferable that the polymerizable monomer be added at most in an amount of not more than 100 parts by weight, or more preferably not more than 50 parts by weight, with respect to 1 part by weight of the titanium oxide particles.

Further, it is preferable that the polymerization temperature at which the polymer base material and the polymerizable monomer are polymerized be at least not less than 40° C., or more preferably not less than 50° C. On the other hand, it is preferable that the polymerization temperature be at most not more than 100° C., or more preferably not more than 80° C.

Further, in order to introduce an active group, e.g., a vinyl group into the polymer base material, it is only necessary to cause the polymer base material and an active-group-containing compound to react in a mixed solution of a catalyst, a polymerization inhibitor, and a solvent. Specific examples of the active-group-containing compound encompass 2-methacryloyloxyethyl isocyanate and hexamethylene diosocyanate. Preferred examples of the solvent encompass polar solvents such as anhydrous dimethyl sulfoxide and anhydrous dimethyl formamide. The polymerization inhibitor is added to inhibit polymerization of active groups introduced into the polymer base material and of active-group-containing compounds. Examples of the polymerization inhibitor encompass hydroquinone. Examples of the catalyst encompass dibutyltin (IV) dilaurate.

It is preferable that the active-group-containing compound be added at least in an amount of not less than 10 wt %, more preferably not less than 50 wt %, or still more preferably not less than 100 wt %, with respect to the polymer base material.

On the other hand, it is preferable that the active-group-containing compound be added at most in an amount of not more than 500 wt %, more preferably not more than 400 wt %, or still more preferably not more than 300 wt %, with respect to the polymer base material.

Moreover, it is preferable that the reaction temperature be at least not less than 30° C., more preferably not less than 40° C., or still more preferably not less than 45° C. On the other hand, it is preferable that the reaction temperature be at most not more than 100° C., more preferably not more than 80° C., or still more preferably not more than 60° C. It should be noted that the reaction time only needs to be set appropriately depending the reaction temperature, etc. Causing a reaction under such conditions as described above makes it possible to easily introduce an active group into the polymer base material.

It is preferable that the rate of introduction (wt %) at which active groups are introduced into the polymer base material be at least not less than 0.1 wt %, more preferably not less than 1.0 wt %, or still more preferably not less than 2.0 wt %. On the other hand, it is preferable that the rate of introduction be at most not more than 30 wt %, more preferably not more than 25 wt %, or still more preferably not more than 20 wt %. If the rate of introduction is higher than 30 wt %, the number of active groups introduced into the polymer base material becomes so large that the active groups may react.

The following describes the step (reactive functional group introducing step) of introducing a reactive functional group into the titanium oxide. A specific example of a method for introducing a reactive functional group is to simply cause a reaction between a silane coupling agent having a reactive functional group and titanium oxide.

The silane coupling agent is described here. The silane coupling agent has such a chemical structure as represented by the following chemical formula:

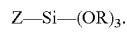

Z—Si—(OR)$_3$.

The "Z" only needs to be a reactive functional group capable of forming a chemical bond with various organic materials such as synthetic resins (polymer base materials or an active group thereof). Specific examples of Z encompass a vinyl group, an epoxy group, an amino group, a (meth)acryloxy group, and a mercapto group. That is, the silane coupling agent for use in the present invention has at least a reactive functional group. Further, the "Si—(OR)$_3$" only needs to be a functional group capable of forming a chemical bond with titanium oxide. Specific examples of OR encompass a methoxy group and an ethoxy group. Further, in the chemical formula, the reactive functional group Z and Si may be bound by a polymer chain, may be bound by a low-molecular chain, or may be bound directly to each other. Further, the three OR's may be identical or different from one another. That is, it is only necessary that at least one of the three OR's be a functional group capable of forming a chemical bond with titanium oxide.

That is, specific examples of the silane coupling agent encompass: vinyl-based silane coupling agents such as vinyltrichlorsilane, vinyltrimethoxysilane, and vinyltriethoxysilane; epoxy-based silane coupling agents such as β-(3,4-epoxycyclohexyl)ethyltrimethoxysilane, γ-glycidoxypropyltrimethoxysilane, γ-glycidoxypropylmethyldimethoxysilane, and γ-glycidoxypropyltriethoxysilane; styryl-based silane coupling agents such as p-styryltrimethoxysilane; methacryloxy-based silane coupling agents such as γ-methacryloxypropylmethyldimethoxysilane, γ-methacryloxypropyltrimethoxysilane, γ-methacryloxypropylmethyldiethoxysilane, and γ-methacryloxypropyltriethoxysilane; acryloxy-based silane coupling agents such as γ-acryloxypropyltrimethoxysilane; amino-based silane coupling agents such as N-β(aminoethyl)γ-aminopropyltrimethoxysilane, N-β(aminoethyl)γ-aminopropylmethyldimethoxymethoxysilane, N-β(aminoethyl)γ-aminopropyltriethoxysilane, γ-aminopropyltrimethoxysilane, γ-aminopropyltriethoxysilane, γ-triethoxy-N-(1,3-dimethyl-butylidene)propylamine, N-phenyl-γ-aminopropyltrimethoxysilane, a hydrochloride salt of N-(vinylbenzyl)-β-aminoethyl-γ-aminopropyltrimethoxysilane, and special amino silane; ureide-based silane coupling agents such as γ-ureidepropyltriethoxysilane; chloropropyl-based silane coupling agents such as γ-chloropropyltrimethoxysilane; mercapto-based silane coupling agents such as γ-mercaptopropyltrimethoxysilane and γ-mercaptopropylmethyldimethoxysilane; sulfide-based silane coupling agents such as bis(triethoxypropyl)tetrasulfide; and isocyanate-based silane coupling agents such as γ-isocyanatepropyltriethoxysilane. Among the silane coupling agents thus taken as examples, γ-methacryloxypropyltrimethoxysilane is preferred in terms of being a polymerizable monomer. The silane coupling agent only needs to be selected appropriately depending on the type of polymer base material, the type of active group of the polymer base material, etc.

As mentioned above, the silane coupling agent has a reactive functional group at one end thereof and a functional group at the other end thereof and, as such, can be suitably used. It should be noted that the reactive functional group is a group capable of reacting with an active group and the functional group is a group capable of reacting with titanium oxide. Further, the following describes an example where an active group is introduced into titanium oxide with use of a silane coupling agent.

Reaction conditions under which to cause a reaction between a silane coupling agent having such a reactive functional group and titanium oxide vary depending on the type of reaction, the type of silane coupling agent that is used, etc. and, as such, are not particularly limited. Further, suitable examples of the type of reaction encompass a dry process and a wet process.

In the case of a dry process, titanium oxide particles are poured into a high-speed stirring machine and a silane coupling agent having a reactive functional group at one end thereof and a functional group at the other end thereof is added to the titanium oxide particles by dropping or spraying. The resultant product is uniformly stirred and then dried. At this time, it is preferable that the silane coupling agent be added in an amount of not less than 0.0001 to not more than 10 parts by weight with respect to 1 part by weight of the titanium oxide particles.

On the other hand, in the case of a wet process, titanium oxide particles and a silane coupling agent are added into an organic solvent and allowed to react at a temperature of room temperature to 150° C. for 10 minutes to 10 days while being stirred. After that, the resultant product is dried after being rid of the solvent and the unreacted silane coupling agent.

Examples of the organic solvent that is used here encompass: hydrocarbon solvents such as toluene and hexane; ether solvents such as tetrahydrofuran and diethylether; and ketone solvents such as acetone and methyl ethyl ketone. It is preferable that the organic solvent be used at least in an amount of not less than 0.1 parts by weight, or more preferably not less than 0.5 parts by weight, with respect to 1 part by weight of the titanium oxide particles (particles of titanium oxide). On the other hand, it is preferable that the organic solvent be used at most in an amount of not more than 1000 parts by weight, or more preferably not more than 50 parts by weight, with respect to 1 part by weight of the titanium oxide particles.

It is preferable that the silane coupling agent be added at least in an amount of not less than 0.0001 parts by weight, or more preferably not less than 0.001 parts by weight, with respect to 1 part by weight of the titanium oxide particles. On the other hand, it is preferable that the silane coupling agent be added at most in an amount of not more than 10 parts by weight, or more preferably not more than 5 parts by weight, with respect to 1 part by weight of the titanium oxide particles. For this, the same reason applies as in the case of a dry process.

It is preferable that the reaction temperature be at least not less than room temperature (25° C.). On the other hand, it is preferable that the reaction temperature be at most not more than 150° C., or more preferably not more than 100° C. For the purpose of long time persistence of the photocatalytic activity of titanium oxide into which a reactive functional group has been introduced by the reactive functional group introducing step, it is preferable that the reaction temperature be approximately 80° C.

Next, the active group introduced into the polymer base material by the active group introducing step and the reactive functional group introduced into the titanium oxide by the reactive functional group introducing step are brought into reaction. Specifically, the adsorption of the titanium oxide into the surface of the polymer base material is caused by the immersion of the polymer base material in a dispersion liquid in which the titanium oxide has been dispersed. Then, the reactive functional group and the active group are brought into reaction. The following describes an example where the polymer base material and the titanium oxide are bound by an amide bond with use of silicone rubber as the polymer base material.

Examples of a dispersion medium in which the titanium oxide is dispersed encompass water and organic solvents such as: hydrocarbon solvents such as toluene and hexane; alcohols; ether solvents such as tetrahydrofuran and diethylether; and ketone solvents such as acetone and methyl ethyl ketone. Among the solvents thus taken as examples, water and alcohols are suitably used for the purpose of dispersing the titanium oxide satisfactorily. Further, for example, in the case of use of a hydrocarbon solvent such as toluene or hexane, the titanium oxide may be dispersed satisfactorily, for example, by stirring the dispersion liquid well with a stirring device such as a stirrer, by using an ultrasonic device, or by using the stirring device and the ultrasonic device together.

In the preparation of the dispersion liquid, it is preferable that the titanium oxide be added at least in an amount of not less than 0.1 wt %, more preferably not less than 0.2 wt %, or still more preferably not less than 0.5 wt %, with respect to the dispersion medium. On the other hand, it is preferable that the titanium oxide be added at most in an amount of not more than 5.0 wt %, more preferably not more than 4.0 wt %, or still more preferably not more than 3.0 wt %, with respect to the dispersion medium.

It is preferable that the reaction temperature at which the reactive functional group of the titanium oxide adsorbed into the surface of the polymer base material and the active group are brought into reaction be at least not less than 25° C., more preferably not less than 50° C., or still more preferably not less than 80° C. On the other hand, it is preferable that the reaction temperature be at most not more than 200° C., more preferably not more than 175° C., or still more preferably not more than 150° C.

It is preferable that after the immersion of the polymer base material in the dispersion liquid and before the reaction, the polymer base material be washed with the same solvent as the dispersion medium. The polymer base material thus immersed has the titanium oxide laminated on the surface thereof. If the polymer base material is brought into reaction without being washed, the polymer base material becomes composite with the titanium oxide remaining laminated. This may impair the properties of the polymer base material or undermine the strength of the polymer base material.

Further, it is possible to perform the reaction under vacuum as needed. The reaction under vacuum of the reactive functional group of the titanium oxide and the active group of the polymer base material makes it possible to produce a titanium oxide composite material faster. In the case of reaction under vacuum, it is preferable that the pressure at which the reaction is performed fall within a range of not less than 0.01 mmHg (1.33 Pa) to not more than 10 mmHg (1.33 kPa).

It should be noted that the reaction conditions for the reacting step and the type of solvent, and the like only need to be changed appropriately depending on the type of polymer base material, the type(s) of reactive functional group and/or active group.

The following describes a method for covering a surface of a polymer base material with titanium oxide via a chemical bond (esp., a method for forming Aspect (ii)). This method is a method for producing a titanium oxide composite material through chemical bonding between a hydroxyl group possessed by titanium oxide and a functional group, possessed by a polymer base material, which is capable of forming a chemical bond with the hydroxyl group, the method including: an introducing step of introducing, into the polymer base material, the functional group capable of forming a chemical bond with the hydroxyl group possessed by the titanium oxide; and a functional group reacting step of causing a reaction between the functional group of the polymer base material and the hydroxyl group possessed by the titanium oxide.

Specific examples of the functional group encompass at least one type of functional group selected from the group consisting of an alkoxysilyl group, an isocyanate group, etc. The functional group on the surface of the polymer base material may be a functional group possessed by a polymer on the surface of the polymer base material, or may be that which has been introduced by modifying the polymer base material by publicly-known means such as acid/alkali treatment, corona discharge, plasma irradiation, surface graft polymerization, etc.

In the introducing step, the functional group capable of forming a chemical bond with the hydroxyl group possessed by the titanium oxide is introduced into the polymer base material. The following describes a case where an alkoxysilyl group is introduced into the polymer base material as the functional group capable of forming a chemical bond with the hydroxyl group possessed by the titanium oxide.

The introduction of the functional group into the polymer base material, i.e., the introducing step only needs to be performed by a publicly-known method and, as such, is not particularly limited. For example, the functional group can be introduced into the polymer base material with use of a silane coupling agent having a functional group at a molecular terminal thereof.

Described here as a method for introducing an alkoxysilyl group into the polymer base material is a method for introducing an alkoxysilyl group into the polymer base material with use of a silane coupling agent. It should be noted that the method for introducing an alkoxysilyl group into the polymer base material is not limited to this method and various methods can be adopted.

A specific example of the method for introducing an alkoxysilyl group into the polymer base material with use of a silane coupling agent may be to directly introduce, into a polymer base material subjected to corona treatment, a silane coupling agent having a functional group at a molecular terminal thereof. Alternatively, a water-insoluble monomer having the functional group can be graft-polymerized directly with the polymer base material by generating radicals by removal of protons (hydrogen atoms) from the polymer base material with use of a surfactant and a peroxide initiator. Use of this method makes it possible to directly introduce, into the polymer base material, a functional group capable of forming a chemical bond with the titanium oxide.

Further, an alkoxysilyl group may be introduced into the polymer base material, for example, by introducing in advance into the polymer base material, an active group capable of reacting with a reactive functional group possessed by the silane coupling agent and then by causing a reaction between the active group and the reactive functional group of the silane coupling agent. It should be noted that specific examples of the active group encompass, but are not limited to, a vinyl group, an amino group, etc. The active group only needs to be set appropriately depending on the type of reactive functional group (Z of the above chemical formula) of the silane coupling agent. Therefore, the silane coupling agent for use in the present embodiment only needs to have at least a functional group or, more preferably, has a functional group and a reactive functional group. It should be noted that the functional group is a group capable of forming a chemical bond with the titanium oxide (or the hydroxyl group possessed by the titanium oxide) and the reactive functional group is a group capable of forming a chemical bond with the active group or the polymer base material.

Described here are specific conditions for a method that uses silk fibroin as the polymer base material, introduces a vinyl group in advance into the silk fibroin as an active group, causes a reaction between the vinyl group and a reactive functional group of a silane coupling agent, and thereby introduces an alkoxysilyl group (Si—OR) into the polymer base material.

The step of introducing the active group into the polymer base material is the same as the active group introducing step mentioned above, and therefore is not detailed here. Next, the active group introduced into the polymer base material and a silane coupling agent having a reactive functional group at one terminal thereof and a functional group at the other terminal thereof are polymerized to introduce an alkoxysilyl group into the polymer base material as a functional group.

The silane coupling agent is not particularly limited, provided it has a functional group and has at a terminal thereof a reactive functional group capable of being polymerized with the active group introduced into the polymer base material. However, in the case of introduction of a vinyl group as the active group, the methacryloxy-based silane coupling agent, e.g., γ-methacryloxypropyltrimethoxysilane can be suitably used. Then, the silane coupling agent and the polymer base material into which the active group has been introduced are brought into polymerization in the presence of a polymerization initiator and a solvent. This makes it possible to introduce an alkoxysilyl group into the polymer base material as a functional group.

Preferably usable examples of the solvent encompass nonpolar organic solvents, e.g., hydrocarbon solvents such as toluene and hexane. Further, examples of the polymerization initiator encompass azobisisobutyronitrile and benzoyl peroxide.

It is preferable that the silane coupling agent be used (added) at least in an amount of not less than 10 wt %, more preferably not less than 50 wt %, or still more preferably not less than 100 wt %, with respect to the polymer base material into which the active group has been introduced. On the other hand, it is preferable that the silane coupling agent be used at most in an amount of not more than 500 wt %, more preferably not more than 400 wt %, or still more preferably not more than 300 wt %, with respect to the polymer base material into which the active group has been introduced.

Further, it is preferable that the polymerization be performed in an atmosphere of nitrogen. It is preferable that the polymerization temperature be at least not less than 40° C., more preferably not less than 45° C., or still more preferably not less than 50° C. On the other hand, it is preferable that the polymerization temperature be at most not more than 80° C., more preferably not more than 75° C., or still more preferably not more than 70° C. It should be noted that the polymerization time only needs to be set appropriately so that a desired rate of introduction (at which functional groups are introduced into the polymer base material) is achieved.

Further, it is preferable that the rate of introduction (wt %) at which functional groups are introduced into the polymer base material be at least not less than 0.1 wt %, or more preferably not less than 1 wt %. The term "rate of introduction" here means the percentage of the silane coupling agent introduced per unit weight of the polymer base material. If the rate of introduction is not less than 0.1 wt %, it is possible to cause the polymer base material to bind to such a sufficient amount of titanium oxide as to be able to express biocompatibility. Meanwhile, the rate of introduction has no particular upper limit. However, if the rate of introduction is higher than 100 wt %, the polymer base material may bind to too large an amount of titanium oxide to be economical.

It should be noted that an alkoxysilyl group can be introduced into the polymer base material not only by the method described above but also by various methods. Further, the reaction conditions are set appropriately depending on the type of polymer base material, the type of active-group-containing compound, the type of silane coupling agent, etc. and, as such, are not particularly limited. Thus, a functional group can be introduced into the polymer base material.

In cases where the functional group is an isocyanate group and where the isocyanate group is introduced into the polymer base material by polymerizing, with the polymer base material, a monomer having the isocyanate group at a terminal thereof, there is a danger that the isocyanate group may be deactivated by reacting with active hydrogen contained in the reaction solvent. In view of this, it is preferable to perform the reaction in a dehydrated solvent such as anhydrous dimethyl sulfoxide or anhydrous dimethyl formamide.

Further, in cases where a monomer having an isocyanate group at a terminal thereof and the polymer base material is brought into reaction (polymerization) in water or alcohol having active hydrogen, it is necessary to protect the isocyanate group, because the isocyanate group reacts with the active hydrogen. Specifically, for example, the polymerization can be performed by protecting the isocyanate group with use of a blocking agent such as phenol, imidazole, oxime, N-hydroxyimide, alcohol, lactam, or an active methylene complex. The blocking agent protecting the isocyanate group can be eliminated by heating. Therefore, the isocyanate group can be introduced into the polymer base material by protecting the isocyanate group by the blocking agent and by heating after polymerization of a monomer at the other terminal and the polymer base material. This makes it possible to obtain a polymer base material having an isocyanate group on a surface thereof.

For example, in the case of use of phenol as the blocking agent, the blocking agent protecting the isocyanate group can be eliminated by heating at a temperature of not less than 110° C. to not more than 120° C. For example, in the case of use of imidazole as the blocking agent, the blocking agent can be eliminated by heating at a temperature of not less than 110° C. to not more than 130° C. For example, in the case of use of oxime as the blocking agent, the blocking agent can be eliminated by heating at a temperature of not less than 130° C. to not more than 150° C. Specific examples of the blocking agent encompass: phenol-containing compounds such as methyl salicylate and methyl-p-hydroxybenzoate; imidazole; and oxime-containing compounds such as methyl ethyl ketone oxime and acetone oxime. Further, depending on the type of polymer base material, it is possible to use: N-hydroxyimide-containing compounds such as N-hydroxyphthalimide and N-hydroxysuccinimide; alcohol-containing compounds such as methoxypropanol, ethylhexanol, pentol, ethyl lactate; lactam-containing compounds such as caprolactam and pyrrolidinone; and active methylene compounds such as ethyl acetoacetate.

In the case of use of isocyanate as the functional group, the other reaction conditions (e.g., the amount of a silane coupling agent that is added with respect to the polymer base material) are the same as in the case where the functional group is an alkoxysilyl group. Therefore, no detailed description is provided.

In the functional group reacting step, a functional group introduced into the polymer base material (e.g., an isocyanate group, an alkoxysilyl group) and a hydroxyl group of the titanium oxide are brought into reaction. This functional group reacting step only needs to be performed under the same conditions as the aforementioned reacting step and, as such, is not detailed here.

It should be noted that the titanium oxide composite material for use in the present invention encompass a titanium oxide composite material produced by laminating a still another compound onto the above-described titanium oxide composite material produced by covering a surface of a polymer base material with titanium oxide. For example, it is possible that a calcium phosphate-based compound such as hydroxyapatite is further laminated onto the titanium oxide composite material produced by covering a surface of a polymer base material with titanium oxide. A calcium phosphate-based compound excels in biostability, and therefore improves biocompatibility when laminated onto the titanium oxide composite material.

Specific examples of a method for further laminating a calcium phosphate-based compound onto the titanium oxide composite material produced by covering a surface of a polymer base material with titanium oxide encompass the following methods (1) to (3):

(1) A method including: applying particles of a mixture of a polymerizable monomer and a calcium phosphate-based compound onto that surface of the titanium oxide composite material, i.e., the titanium oxide composite material produced by covering a surface of a polymer base material with titanium oxide, on which titanium oxide exists; and polymerizing and solidifying the polymerizable monomer with heat, light, radiation, etc.

(2) A method for depositing a calcium phosphate-based compound by immersing, in a solution containing calcium ions and phosphate ions, the titanium oxide composite material produced by covering a surface of a polymer base material with titanium oxide.

(3) A method for depositing a calcium phosphate-based compound by alternately immersing, in a solution containing calcium ions and a solution containing phosphate ions, the titanium oxide composite material produced by covering a surface of a polymer base material with titanium oxide.

Further, in the case of the method (1), use of a mold having the desired shape makes it possible to laminate the calcium phosphate-based compound so that the calcium phosphate-based compound takes the desired shape.

(1-2. Medical Device That is Covered with the Titanium Oxide Material)

An example of the medical device whose surface is covered with the titanium oxide material is an implantable medical device, an extracorporeal-intracorporeal medical device, or a body surface contact medical device. The implantable medical devices is a medical devices that is implanted into a body. Examples of the implantable medical device encompass artificial hearts, pacemakers, implantable defibrillators, artificial valves, artificial valve rings, artificial blood vessels, stents, artificial joints, artificial heads, internal fixators, mini microplate systems, external wound fixators, spinal fusion systems, artificial ligaments, artificial bones, artificial noses, artificial pharynges, artificial anuses, artificial bladders, and artificial cochleae. Further, the extracorporeal-intracorporeal medical device is a medical device that passes in and out of the body. Examples of the extracorporeal-intracorporeal medical device encompass catheters, tubes, catheter access ports, gastrostomy tubes, shunt valves, neurosurgical drainage tubes, and blood accesses. Further, the body surface contact medical device is a medical device that is used in contact with a body surface. Examples of the body surface contact medical device encompass wound dressings. Beside the above, a medical device such as an infusion filter can be applied in the present invention.

By covering the surface of an implantable medical device or an extracorporeal-intracorporeal medical device with the titanium oxide material and irradiating the titanium oxide material with ultrasonic waves to exert bactericidal action, bacterial infection can be prevented from occurring when the medical device is implanted into the body. Further, even in cases where inflammation due to bacterial infection is caused in the vicinity of the surface of the medical device after the implantation of the medical device, the medical device can be sterilized without being removed, because bactericidal action can be exerted by irradiating the body with ultrasonic waves extracorporeally. Further, since the surface of the medical device irradiated with ultrasonic waves brings about an angiogenesis-stimulating effect, the surface of the medical device also bring about a healing-promoting effect. The surface of the medical device irradiated with ultrasonic waves also brings about an effect of degrading a blood clot and a biofilm.

As for a body surface contact medical device, the same bactericidal effect and healing-promoting effect as above are obtained. Further, a medical device, such an infusion filter, that does not make direct contact with the body, can be subjected to bacteria elimination, antibacterial treatment, or sterilization by ultrasonic irradiation. In particular, an infusion filter can be rid of bacteria even during an intravenous drip. Further, even a medical device having such a structure making bacterial elimination difficult can sterilized without being disassembled.

The surface of the medical device is covered with the titanium oxide material as described above. However, it is possible, for example, that after the medical device is coated with a polymer such as silicone, the titanium oxide is adsorbed physically into or bound chemically to a surface of the polymer. Furthermore, it is preferable that the medical device be a medical device whose surface has been covered with the titanium oxide material by flocking. In such a medical device whose surface has been covered with the titanium oxide material by flocking, the titanium oxide (esp., in the form of particles or short fibers) covers the surface of the medical device so as to be raised. This means that the titanium oxide, which exerts bactericidal action and an angiogenesis-stimulating effect when irradiated with ultrasonic waves, covers the surface of the medical device at high density over a large surface area. This brings about more advantageous effects (such as a bactericidal effect and an angiogenesis-stimulating effect) than in cases where the titanium oxide material covers the surface of the medical device in a planar state.

The surface of the medical device can be covered with the titanium oxide by flocking, e.g., a publicly-known flocking process. For example, the surface of the medical device may be covered with the titanium oxide by flocking by applying a method described in "Iinuma, N: *Shin Kôbunshi Bunko* 17: *Furokku Kakô no Jissai* (*New Polymer Paperback* 17: *Practice of Flocking*), Koubunshikankoukai, Aug. 1, 1979", "Unexamined Japanese Patent Application Publication No. 116557/1995 (Tokukaihei 7-116557; published on May 9, 1995)", "Japanese Translation of PCT Patent Application Publication No. 505845/2000 (Tokuhyo 2000-505845; published on May 16, 2000)", "Unexamined Japanese Patent Application Publication No. 141926/1994 (Tokukaihei 6-141926; published on May 24, 1994)", or Japanese Unexamined Patent Application Publication No. 38596/2003 (Tokukai 2003-38596; published on Feb. 12, 2003).

In particular, the method and apparatus described in International Publication No. 2007/061100 Pamphlet (published on May 31, 2007) are preferred because they make it possible to efficiently cover the surface of the medical device with the titanium oxide material by flocking. International Publication No. 2007/061100 Pamphlet describes a method, including the steps of: placing a substrate for a medical device between a first electrode and a second electrode, the substrate having a surface to which an adhesive has been applied; mounting short titanium oxide fibers on the second electrode; rotating the medical device substrate; and applying a voltage to the first electrode and the second electrode, wherein the first electrode and the medical device substrate are in electrical connection with each other. According to the method, Coulomb's force causes the short titanium oxide fibers on the second electrode to fly toward the first electrode. At this time, the short titanium oxide fibers adhere to the surface of the medical device substrate, placed between the first electrode and the second electrode, whose surface has the adhesive applied thereto. Further, since the first electrode and the medical device substrate are in electrical connection with each other, the short titanium oxide fibers on the surface of the medical device substrate gain electromotive force that raises the short titanium oxide fibers. This makes it possible to efficiently cover the surface of the medical device with the titanium oxide material by flocking. According to the method, it is preferable that each of the short titanium oxide fibers take the shape of a column or sphere having a longer length of not less than 1 µm to less than 1 cm (more preferably not less than 5 µm to less than 5 mm, or most preferably not less than 50 µm to less than 1 mm) and a shorter length of not less than 1 nm to less than 1 mm (more preferably not less than 10 nm to less than 0.5 mm, or most preferably not less than 100 nm to less than 0.1 mm).

It should be noted that the "titanium oxide coated medical device" of the ultrasonic medical apparatus encompasses the titanium oxide per se or the titanium oxide composite material per se. Furthermore, the ultrasonic medical apparatus of the present invention and the medical device constituting the same are targeted not only at humans but also at nonhuman mammals (e.g., monkeys, dogs, cats, cattle, pigs, sheep, mice, rats, rabbits, etc.).

FIG. 1 shows an example of an arrangement of an ultrasonic medical apparatus according to an embodiment of the present invention. It should be noted that the present invention is not limited to this. In FIG. 1, the titanium oxide coated medical device (10) is constituted by a catheter (12) and a percutaneous device (11). In the present embodiment, the percutaneous device (11) has a surface coated with a titanium oxide material. The percutaneous device (11) of FIG. 1 is intended to serve as a percutaneous terminal by which the catheter (12) is fixed at the location in a living organism into which the catheter (12) has been inserted. Moreover, the percutaneous device (11) is implanted under the skin (30) (i.e., in the body). Bactericidal action and an angiogenesis-stimulating effect are exerted by irradiating the percutaneous device (11) with ultrasonic waves.

Although the titanium oxide coated medical device (10) of the ultrasonic medical apparatus (100) of FIG. 1 is such that only the surface of the percutaneous device (11) constituting the titanium oxide coated medical device (10) is covered with the titanium oxide material, the present invention is not limited to this. The catheter (12), as well as the percutaneous device (11), may be covered with the titanium oxide. That is, the surface of the titanium oxide coated medical device of the ultrasonic medical apparatus of the present invention may be entirely covered with the titanium oxide material, but does not necessarily need to be entirely covered with the titanium oxide material. It is possible to cover, with the titanium oxide material, only a component required to exert bactericidal action and an angiogenesis-stimulating effect when irradiated with ultrasonic waves.

<2. Ultrasonic Irradiation Means>

The "ultrasonic irradiation means", which constitutes the ultrasonic medical apparatus of the present invention, is means for irradiating the titanium oxide coated medical device with ultrasonic waves. The ultrasonic irradiation means can generate ultrasonic waves capable of causing the titanium oxide coated medical device to exert bactericidal action, an angiogenesis-stimulating effect, and an effect of degrading a blood clot and a biofilm, etc. The ultrasonic irradiation means is not particularly limited, provided it is arranged so as to be able to irradiate the titanium oxide coated medical device with such ultrasonic waves. In other words, the ultrasonic irradiation means only needs to be able to generate ultrasonic waves with such an output as to cause the titanium oxide coated medical device to exert bactericidal action, an angiogenesis-stimulating effect, and an effect of degrading a blood clot and a biofilm, etc. The output varies depending on the type of titanium oxide material for the titanium oxide coated medical device to be irradiated, the rate of coverage at which the titanium oxide coated medical device is covered with the titanium oxide material, and the condition and location of installation of the titanium oxide coated medical device. Therefore, it is only necessary to adopt an optimum output after consideration. The output is not particularly limited; however, it is preferable that the output be not more than 1 W/cm$^2$, or more preferably approximately 0.2 W/cm$^2$, in terms of spatial peak-temporal average intensity $I_{SPTA}$.

Further, since the ultrasonic irradiation means irradiates living organisms such as human bodies with ultrasonic waves, it is preferable that the ultrasonic irradiation means be means capable of radiating ultrasonic waves with an output falling within safety standards for living organisms. The term "safety standards for living organisms" here means such an output that the safety of living organisms, if any, irradiated with ultrasonic waves is guaranteed. The output of ultrasonic waves within the safety standards for living organisms varies depending on living organisms to be irradiated, and therefore is not limited. It should be noted that the safety standards of ultrasonic waves for human bodies are defined, for example, by the Japan Society of Ultrasonics in Medicine. In the case of continuous waves, the spatial peak-temporal average intensity $I_{SPTA}$ is 1 W/cm$^2$. The above intensity can be measured by a method (radiation pressure or hydrophone method) described in "Chô-onpa Binran (*Ultrasound Handbook*)" (Ultrasound Handbook Editorial Committee ed., Maruzen Co., Ltd., 1999, pp. 41-46. (ISBN 4-621-04633-0). It should be noted that the output of the ultrasonic irradiation means may be fixed or adjustable. However, it is preferable that the output of the ultrasonic irradiation means be adjustable, because such an arrangement makes it possible to adjust the output in accordance with the safety standards for objects to be irradiated.

The inventors' studies show that a higher output of irradiation of titanium oxide tends make it easier to obtain an bactericidal effect and an antibacterial effect and that a comparatively lower output tends to make it easier to obtain an angiogenesis-stimulating effect. The threshold output varies depending on the type of titanium oxide material for the titanium oxide coated medical device to be irradiated, the rate of coverage at which the titanium oxide coated medical device is covered with the titanium oxide material, and the condition and location of installation of the titanium oxide coated medical device. Therefore, it is only necessary to adopt an optimum threshold output after consideration. The threshold output is not particularly limited. For example, the threshold output is 0.4 W/cm$^2$ in terms of spatial peak-temporal average intensity $I_{SPTA}$.

Further, it is preferable that the ultrasonic irradiation means be means capable of generating one or more types of ultrasonic waves selected from the group consisting of continuous waves, pulse waves, burst waves, and standing waves. Irradiation of the titanium oxide with continuous waves makes it possible to excite the titanium oxide continuously in terms of time. This makes it possible to greatly reduce the amount of ultrasonic irradiation time required to cause the titanium oxide coated medical device to exert bactericidal action, an angiogenesis-stimulating effect, and an effect of degrading a blood clot and a biofilm, etc. The use of pulse waves or burst waves make it possible to intermittently radiate ultrasonic waves with a high output to some extent (that is, the adjustment of duty ratios makes it possible to repeat irradiation cycles each containing, with an appropriate ratio, a period of time during which ultrasonic waves are radiated and a period of time during which ultrasonic irradiation is paused). Therefore, even in cases where the use of continuous waves may undesirably cause an increase in body surface temperature of a living organism, the use of pulse waves or burst waves make it possible to cause the titanium oxide coated medical device to exert bactericidal action, an angiogenesis-stimulating effect, and an effect of degrading a blood clot and a biofilm, etc. while inhibiting an increase in body surface temperature of the living organism due to ultrasonic irradiation. The generation of standing waves in the vicinity of the titanium oxide coated medical device by the ultrasonic irradiation means causes nodes and antinodes to be generated at spatially fixed locations. All the antinodes require the same amount of time for maximum ultrasonic amplitude; at the same time, a perfect standing wave shows amplitude twice as high as incident ultrasonic amplitude. This brings about an effect of fixing the irradiation location and halving the ultrasonic output intensity.

It is preferable that the ultrasonic irradiation means be means capable of generating, in a single transmission, ultrasonic waves containing higher harmonic waves or multi-frequency waves. Irradiation with a mixture of higher harmonic waves or multi-frequency waves in a single transmission brings about an effect of promoting enhancement of sound intensity in the vicinity of the titanium oxide coated medical device in accordance with the resonant properties of the titanium oxide coated medical device, and such an effect can be used to cause the titanium oxide coated medical device to exert bactericidal action, an angiogenesis-stimulating effect, an effect of degrading a blood clot and a biofilm, etc.

Further, the "means capable of generating, in a single transmission, ultrasonic waves containing multi-frequency waves" makes it possible to modulate the amplitude of an ultrasonic wave signal S1 by adding the ultrasonic wave signal S1 to a low-frequency ultrasonic wave signal S2 (S1+S2) or by multiplying the ultrasonic wave signal S1 by the low-frequency ultrasonic wave signal S2 (S1×S2) and transmit, in a single transmission, an ultrasonic wave signal containing multi-frequency waves (S1 and S2) generated as a result of the modulation. It should be noted here that the ultrasonic wave signal S1 has one or more frequency components for use in excitation of titanium oxide and the low-frequency ultrasonic wave signal S2 is used for in vivo propagation. Thus, even in cases where in vivo ultrasonic attenuation is so large that S1 alone cannot cause ultrasonic waves to reach a deeply-situated titanium oxide coated medical device, irradiation with ultrasonic waves containing multi-frequency waves (S1 and S2) enables the S1 component to reach the medical device together with the S2 component, having small in vivo ultrasonic attenuation all the more because of its low frequency, which reaches the deeply-situated titanium oxide coated medical device. This makes it possible to cause the titanium oxide coated medical device to exert bactericidal action, an angiogenesis-stimulating effect, an effect of degrading a blood clot and a biofilm, etc.

Although the ultrasonic irradiation means only needs to be means capable of generating one or more types of ultrasonic waves selected from the group consisting of continuous waves, pulse waves, burst waves, and standing waves, it is preferable that the ultrasonic irradiation means be means capable of changing from outputting one type of ultrasonic wave to outputting another type of ultrasonic wave. Further, it is preferable that the ultrasonic irradiation means be means capable of changing, in a single transmission, from generating ultrasonic waves containing higher harmonic waves to generating ultrasonic waves containing multi-frequency waves, and vice versa. This is because it is useful in using the ultrasonic medical apparatus of the present invention to be able to change the type of ultrasonic wave appropriately in accordance with different purposes of ultrasonic irradiation and different targets of ultrasonic irradiation.

In the ultrasonic medical apparatus of the present invention, it is preferable that the ultrasonic irradiation means be means capable of radiating focused ultrasonic waves. The focusing of ultrasonic waves upon a local domain of the titanium oxide to be irradiated makes it possible to excite only that portion of the titanium oxide which is to be irradiated and make the output of ultrasonic waves locally dense. Therefore, OH radicals can be generated efficiently to exert bactericidal action, an angiogenesis-stimulating effect, etc., while the safety of living organisms is assured by low-voltage application. The present invention is not limited in its specific arrangement, provided that it is arranged so as to be able to radiate focused ultrasonic waves as described above. An example is an arrangement in which, as shown in FIG. 1, the surface of the oscillation element (27) of the ultrasonic probe (21) is designed to have such a curvature as to maximize sound output density at the focal point (31). The curvature only needs to be set appropriately in accordance with the focal length. Beside the above, in cases where the surface of the oscillation element (27) of the ultrasonic probe (21) is flat, an acoustic lens having a curvature may be used to focus ultrasonic waves by refraction. The curvature only needs to be set appropriately in accordance with the desired focal length, the sound speed of a material for the acoustic lens, and the sound speed, for example, of a skin or a coupler that makes contact with a surface of the acoustic lens. The ultrasonic medical apparatus of the present invention does not necessarily need to be arranged so as to be able to radiate focused ultrasonic waves, provided that it brings about the effects of the present invention.

Further, in the ultrasonic medical apparatus of the present invention, it is preferable that the ultrasonic irradiation means include a coupler so as to be able to cause ultrasonic waves to efficiently enter a living organism via the skin (such a coupler being referred to also as "acoustic matching coupler"). In the ultrasonic medical apparatus (100) of FIG. 1, the ultrasonic probe (21) is provided with a coupler (22) so as to be able to cause ultrasonic waves to efficiently enter the living organism via the skin (30). Preferably usable examples of material for the coupler encompass silicone. In the ultrasonic medical apparatus (100) of FIG. 1, the space (28) between the coupler (22) and the oscillation element (27) is filled with degassed water so that ultrasonic waves can be transmitted without a loss to that surface of the coupler (22) which makes contact with the skin (30). The reason for the use of degassed water is to prevent bubbles from being generated due to ultrasonic irradiation. In the present invention, the fluid that fills the interior of the coupler is not limited to degassed water. For example, it is possible to use a coupler filled with material, such as silicone or urethane, which is suitable to serve as an ultrasonic propagation medium between the oscillation element of the ultrasonic probe and the living organism.

The ultrasonic medical apparatus of the present invention is not particularly limited in a transducer constituting the ultrasonic irradiation means; however, it is preferable that the transducer be composed of a piezoelectric substance having excellent electro-acoustic transducer properties. The term "piezoelectric substance having excellent electro-acoustic transducer properties" here means, but is not particularly limited to, a piezoelectric substance having a coefficient of electromechanical coupling of not less than 10% (more preferably not less than 30%, or still more preferably not less than 60%). Examples of the piezoelectric substance having a coefficient of electromechanical coupling of not less than 10% encompass a rock crystal (which has a coefficient of electromechanical coupling of 11%), a water-soluble crystal (which has a coefficient of electromechanical coupling of 38%, in the case of lithium sulfate), a piezoceramic (which has a coefficient of electromechanical coupling of 45% to 70%), a highly-bound piezoelectric crystal (which has a coefficient of electromechanical coupling of 55%), a polymeric piezoelectric material (which has a coefficient of electromechanical coupling of 30%), a composite piezoelectric material (which has a coefficient of electromechanical coupling of 45% to 70%), and electrodeposited piezoelectric material (which has a coefficient of electromechanical coupling of 31% to 37%) (see *Kaitei Iyô Chô-onpa Kiki Handobukku* (*Revised Handbook of Medical Ultrasound Equipment*), Electronic Industries Association of Japan ed., Corona Publishing Co., Ltd., 1997, pp. 24 (ISBN 4-339-07067-X)). It should be noted here examples of the "piezoceramic" encompass $BaTiO_3$, PZT (lead zirconate titanate), PCM (see *Kaitei Iyô Chô-onpa Kiki Handobukku* (*Revised Handbook of Medical Ultrasound Equipment*), Electronic Industries Association of Japan ed., Corona Publishing Co., Ltd., 1997, pp. 24 (ISBN 4-339-07067-X)), and PLZT (lead lanthanum zirconate titanate). Further, examples of the "highly-bound piezoelectric crystal" encompass $LoNbO_3$, $LiTaO_3$, and $LiGaO_3$. Further, examples of the "water-soluble crystal" encompass ADP (ammonium dihydrogen phosphate), KDP (potassium dihydrogen phosphate), EDT (ethylenediamine tartrate), DKT (dipotassium tartrate), and LH (lithium sulfate). Further, examples of the "electrodeposited piezoelectric material" include CdS, ZnO, and GaAs. Further, examples of the "polymer piezoelectric material" encompass PVDF (polyvinylidene fluoride). In the ultrasonic medical apparatus of the present invention, the transducer may be composed of any one of the foregoing piezoelectric substances or any combination thereof.

Further, in the ultrasonic medical apparatus of the present invention, it is preferable that the ultrasonic irradiation means be means capable of generating ultrasonic waves (high-frequency waves) at a frequency of not less than 150 kHz (or more preferably not less than 500 kHz). In comparison with the use of low-frequency ultrasonic waves, the use of high-frequency ultrasonic waves makes it possible to narrow the width of an ultrasonic beam with improved directivity in an ultrasonic field. This makes it possible to irradiate only localized titanium oxide with ultrasonic waves. This brings about an effect of inhibiting excessive irradiation of a region that does not require irradiation, e.g., a region free of titanium oxide and thereby enhancing the safety of living organism and the efficiency of irradiation.

FIG. 1 shows an example of an arrangement of an ultrasonic medical apparatus according to an embodiment of the present invention. In FIG. 1, the ultrasonic irradiation means (20) includes an ultrasonic probe (21), a coupler (22), a waveform generator (23), an RF signal amplifier (24), a junction cable (25), and a transmission cable (26).

The ultrasonic irradiation means (20) of the ultrasonic medical apparatus (100) is arranged such that the ultrasonic probe (21), the coupler (22), the waveform generator (23), the RF signal amplifier (24), the junction cable (25), and the transmission cable (26) are separate components. However, the present invention is not limited to this. The ultrasonic probe (21), the coupler (22), the waveform generator (23), the RF signal amplifier (24), the junction cable (25), and the transmission cable (26) may be wholly or partially integrated. Furthermore, the ultrasonic medical apparatus of the present invention may include components other than the foregoing components. If the waveform generator (23) can by itself output a voltage sufficient to exert effect, the RF signal amplifier (24) may be omitted.

The ultrasonic probe (21) is a member for irradiating, with ultrasonic waves, the implanted titanium oxide coated medical device (10). The waveform generator (23) generates a continuous-wave, pulse-wave, or burst-wave electrical signal to be applied to the ultrasonic probe (21). The continuous-wave, pulse-wave, or burst-wave electrical signal thus generated is inputted to the RF signal amplifier (24) via the junction cable (25) and then amplified by the RF signal amplifier (24). The electrical signal thus amplified is inputted to the ultrasonic probe (21) via the transmission cable (26). The electrical signal thus inputted is converted into sound waves by the surface of the oscillation element (27) provided in the ultrasonic probe (21) and then outputted as ultrasonic waves.

After the process, the percutaneous device (11), covered with the titanium oxide material, of the implanted titanium oxide coated medical device (10) is entirely irradiated with ultrasonic waves. This makes it possible to obtain an antibacterial effect, an effect of stimulating angiogenesis induced by cytokines secreted from the surrounding tissue, an anti-infective effect based on the stimulation of angiogenesis or an anti-infective effect based on the degradation a blood clot and a biofilm, and a healing effect.

It should be noted that the ultrasonic irradiation means of the present invention can be realized by a normal medical ultrasonic apparatus. For example, a medical ultrasonic diagnostic apparatus can be used, provided it can output sound power sufficient to exert effect.

<3. How to Use the Ultrasonic Medical Apparatus of the Present Invention>

The ultrasonic medical apparatus of the present invention only needs to be used by using the ultrasonic irradiation means to irradiate the implanted titanium oxide coated medical device with ultrasonic waves. There is no particular limit on specific conditions such as the output of ultrasonic waves to be radiated, the frequency, the irradiation time, and the type of ultrasonic wave (continuous wave, pulse wave, burst wave, and standing wave). It is only necessary to adopt optimum conditions in consideration purposes and target living organisms.

In cases where the titanium oxide coated medical device is used as an implantable medical device (such as an artificial heart, a pacemaker, an implantable defibrillator, an artificial valve, an artificial valve ring, an artificial blood vessel, a stent, an artificial joint, an artificial femoral head, an internal fixator, a mini microplate system, an external wound fixator, a spinal fusion system, an artificial ligament, an artificial bone, an artificial nose, an artificial pharynge, an artificial anus, an artificial bladder, or an artificial cochlea) or as an extracorporeal-intracorporeal medical device (such as a catheter, a tube, a catheter access port, a gastrostomy tube, a shunt valve, a neurosurgical drainage tube, or a blood access) and where inflammation attributable to bacterial infection is caused in the vicinity of the titanium oxide coated medical device after implantation of the titanium oxide coated medical device, it is only necessary to exert bactericidal action by irradiating the titanium oxide coated medical device with ultrasonic waves extracorporeally. This makes it possible to sterilize the titanium oxide coated medical device without removing the titanium oxide coated medical device.

Further, by covering an affected area of the body with a wound dressing covered with the titanium oxide material and irradiating the wound dressing with ultrasonic waves, the effect of stimulating angiogenesis in the vicinity of the affected area is obtained, with the result that the effect of promoting healing is also obtained.

Ultrasonic irradiation of an infusion filter covered with the titanium oxide material makes it possible to eliminate bacteria even during an intravenous drip.

Even a medical device having such a structure making bacterial elimination difficult can be subjected to bacterial elimination or sterilization without disassembly by covering the medical device with the titanium oxide material and irradiating the medical device with ultrasonic waves.

EXAMPLES

The embodiments of the present invention will be fully described below by way of Examples. The present invention is not limited to these Examples. As for details, it is needless to say that various aspects are possible.

Example 1

Methodology

In order to evaluate the generation of OH radicals by ultrasonic irradiation of a titanium oxide composite material, a focusing-type ultrasonic probe, made of lead zirconate titanate ("PZT"), which has a resonant frequency of 500 kHz, an aperture element diameter of 40 mm, and a curvature radius (focal length) of 30 mm was prepared (see the ultrasonic probe (21) of FIG. 1 for the constitution thereof). The ultrasonic probe was designed in consideration of the required sound output intensity and the required width of a beam in the focal area, and the frequency and the aperture diameter were determined by means of numerical simulations in consideration of the properties of piezoelectric materials. Further, the focal length was selected in consideration of irradiation of a superficial part of the skin. As a result of using a pressure-sensitive paper method "*Chô-onpa Binran* (*Ultrasound Handbook*)" (Ultrasound Handbook Editorial Committee ed., Maruzen Co., Ltd., 1999, pp. 471. (ISBN 4-621-04633-0) to examine, as the acoustic field properties of the ultrasonic probe thus prepared, the beam width defined as a half-value width 6 dB lower than the sound pressure level on the central axis, the beam width was 5.8 mm. Thus, it was confirmed that the ultrasonic probe has been prepared substantially as designed.

Figure 2:
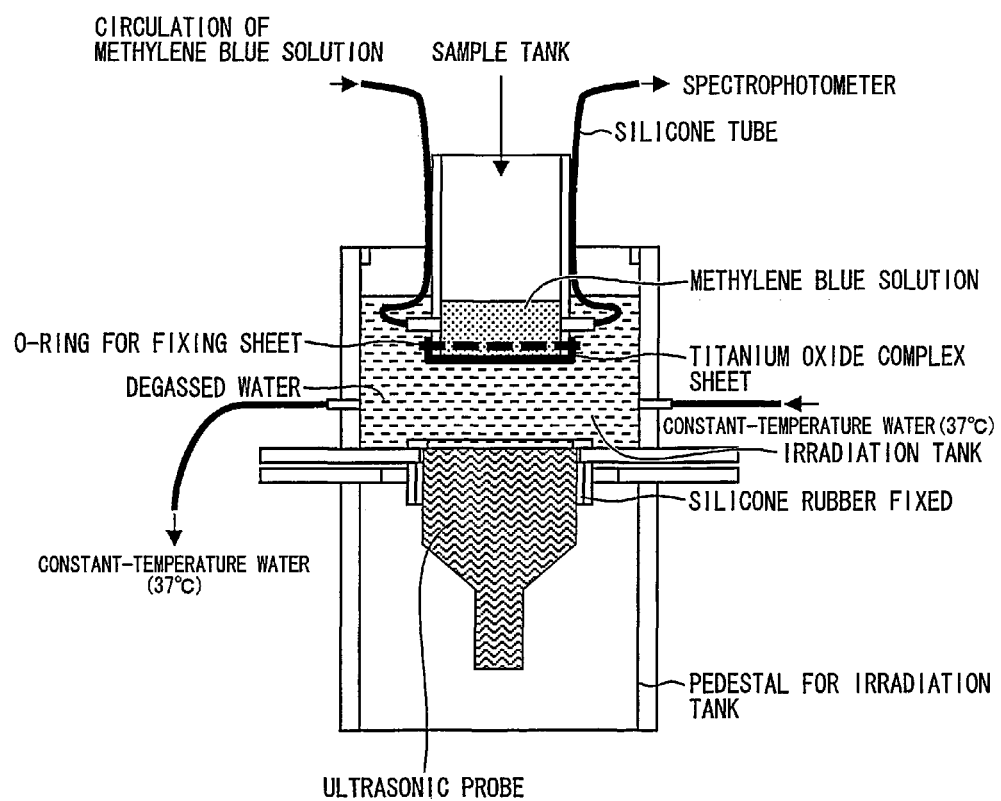
FIG. 2 schematically shows an experimental apparatus used in Examples.

FIG. 2 schematically shows an experimental system built to evaluate the generation of OH radicals with use of the ultrasonic probe thus prepared. In the present example, a sheet of titanium oxide complex (hereinafter referred to as "titanium oxide complex sheet") described in Examples of Japanese Unexamined Patent Application Publication No. 143417/2004 (Tokukai 2004-143417; published on May 20, 2004) was used as a titanium oxide composite material. The titanium oxide complex sheet was produced in the following manner.

(Method for Producing the Titanium Oxide Complex Sheet)

Titanium oxide particles (particle diameter of 200 nm to 300 nm, anatase-type, specific surface of 5 $m^2/g$; manufactured by Ishihara Sangyo Kaisha Ltd.) were dried at 120° C. for 24 hours. After that, 5.0 g of the titanium oxide particles, 150 ml of anhydrous toluene, and 5.0 ml of γ-aminopropyltriethylsilane (manufactured by Shin-Etsu Silicone Co., Ltd.; numbered KBE-903) were poured into a three-necked flask having a capacity of 300 ml and then refluxed at 120° C. for 6 hours, with the result that aminated titanium oxide was obtained by introducing amino groups into titanium oxide. The aminated titanium oxide thus obtained was purified by spinning down with a large amount of toluene and then dried at 60° C. all day and night.

Meanwhile, a surface of a 0.3-mm-thick silicone rubber sheet serving as a polymer base material was treated by corona discharge. Then, the silicone rubber and 25 ml of 10 wt % aqueous solution of acrylic acid were poured into a polymerization tube, deaerated under reduced pressure, and then polymerized at 60° C. for 1 hour with the polymerization tube sealed, with the result that acrylic acid was grafted onto the surface of the silicone rubber. Thus, a silicone rubber sheet (carboxyl-group-introduced silicone rubber sheet) was obtained by introducing carboxyl groups onto the surface of the silicone rubber.

Then, 40 mg of the aminated titanium oxide particles, into which the amino groups have been introduced, were dispersed well in 20 ml of distilled water, with the result that a dispersion liquid was obtained. After that, the carboxyl-group-introduced silicone rubber sheet, which had been cut into the shape of a circle having a diameter of 1.5 cm, was immersed in the dispersion liquid and left intact for 1 hour, with the result that the titanium oxide particles were adsorbed into the surface of the carboxyl-group-introduced silicone rubber sheet. After that, the carboxyl-group-introduced silicone rubber sheet, into which the titanium oxide particles had been adsorbed, was withdrawn and then washed with running water for a long time. Then, the carboxyl-group-introduced silicone rubber sheet thus washed was heated at 180° C. under reduced pressure of 1 mmHg for 6 hours to form an amide bond, with the result that the titanium oxide complex sheet was obtained.

(Depigmentation Test)

The experimental system of FIG. 2 was used to conduct a depigmentation test to quantitatively evaluate the power of oxidative degradation by OH radicals. The depigmentation test was conducted with reference to "Okada, K., Kudo, N., and Yamamoto, K.: *Collection of Abstracts of the 80th Annual Scientific Meeting of the Japan Society of Ultrasonics in Medicine*, pp. 333, 2007". The depigmentation test was conducted by using a diluted methylene blue solution as a pigment aqueous solution. The titanium oxide complex sheet was attached firmly to a lower surface of a cylindrical sample tank having a diameter of 30 mm. The methylene blue solution was poured into the sample tank and left intact until the pigment was adsorbed sufficiently into the sheet. After that, the pigment degradation ability was evaluated by ultrasonic irradiation. The ultrasonic irradiation was performed under the following conditions: continuous waves; a frequency of 500 kHz; a voltage of 10V; and a sound output intensity of 0.6 $W/cm^2$. It should be noted that this sound intensity sufficiently satisfies the safety standards (1 $W/cm^2$) for continuous-wave output as defined by the Japan Society of Ultrasonics in Medicine. The irradiation time was 240 minutes at a maximum.

In this case, the space between the surface of the ultrasonic probe and the surface of the titanium oxide complex sheet was filled with degassed water. For the convenience of avoiding loss in sound output due to the adhesion of bubbles to the surface of the ultrasonic prove by prolonged intermittent ultrasonic irradiation, the ultrasonic probe was disposed upward with respect to the direction of gravitational force. Further, for the purpose of eliminating the possibility of an influence on pigment degradation by an increase in temperature of the degassed water and the methylene blue solution, the temperature of degassed water contained in an irradiation tank was controlled by circulation of hot water from a constant-temperature bath so that the temperature was held constant at approximately 37° C. The methylene blue solution was deaerated, too.

With the degradation of pigment by OH radicals, the degree of transparency of the methylene blue solution became higher. This phenomenon was measured with use of a spectrophotometer (VT650ST; manufactured by JASCO Corporation). The experiment was conducted with the system arranged to perform a process by which the spectrophotometer sucks in minute amounts of samples of the methylene blue solution from the sample tank at intervals of 10 minutes and refluxes the samples into the sample tank after determination of absorbance. This made it possible to continuously trace a change over time in absorbance of the methylene blue solution.

Depigmentation tests were conducted to trace changes over time in absorbance in four patterns (namely (1) US(−)AmTiO$_2$(−), (2) US(+)AmTiO$_2$(−), (3) US(−)AmTiO$_2$(+), and (4) US(+)AmTiO$_2$(+)) from among combinations of the presence or absence of ultrasonic irradiation ("US") and the presence or absence of a titanium oxide complex sheet ("AmTiO$_2$") and then evaluate the ability of generating OH radicals. It should be noted that (+) denotes presence and (−) denotes absence. Further, AmTiO$_2$(−) denotes an untreated silicone sheet that is not covered with titanium oxide. Since (1) US(−)AmTiO$_2$(−) means leaving the methylene blue solution intact, it was treated as having no change in absorbance.

<Results>

Figure 3:
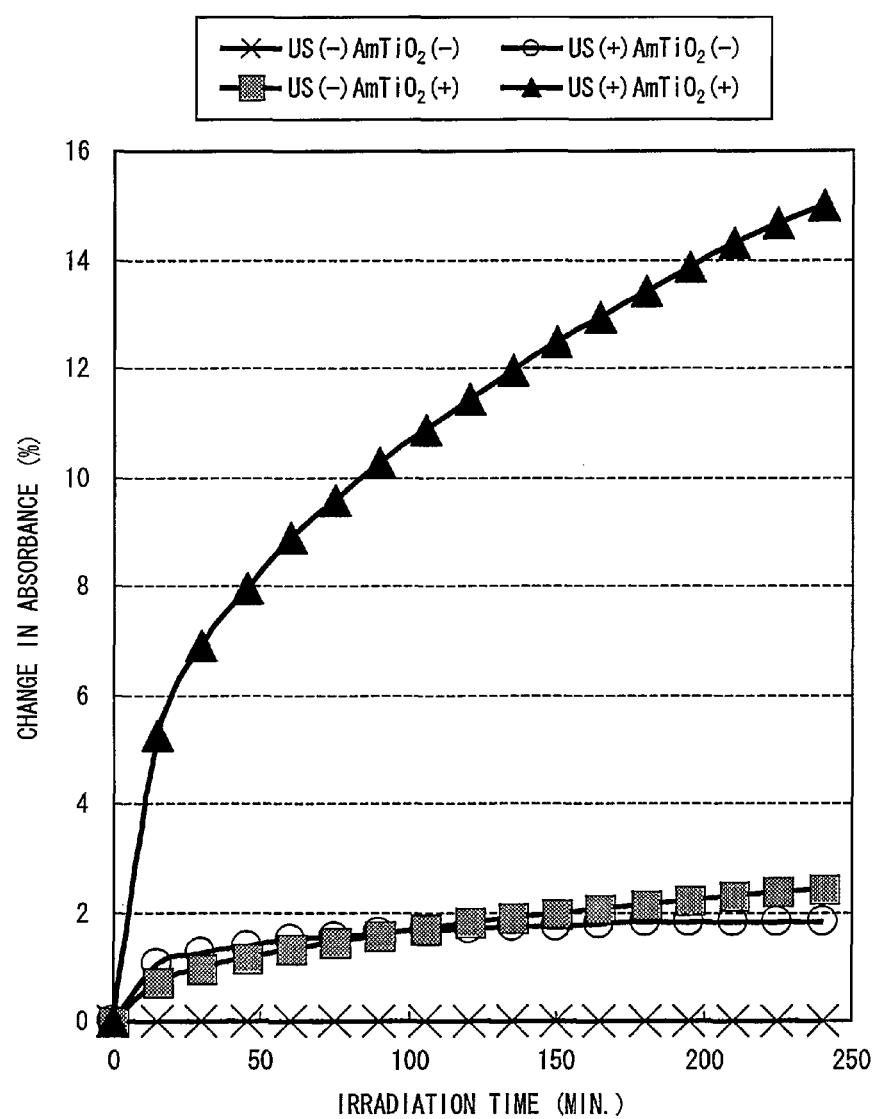
FIG. 3 is a graph, showing results of depigmentation tests conducted in Example 1, on which "US(−)AmTiO$_2$(−)", "US(+)AmTiO$_2$(−)", "US(−)AmTiO$_2$(+)", and "US(+)AmTiO$_2$(+)" represent a result obtained by using an untreated silicon sheet and without ultrasonic irradiation, a result obtained by using an untreated silicon sheet and with ultrasonic irradiation, a result obtained by using a titanium oxide complex sheet and without ultrasonic irradiation, and a result obtained by using a titanium oxide complex sheet and with ultrasonic irradiation, respectively.

FIG. 3 shows results of the depigmentation tests. In FIG. 3, results of the four patterns are represented by (1) US(−)AmTiO$_2$(−), (2) US(+)AmTiO$_2$(−), (3) US(−)AmTiO$_2$(+), and (4) US(+)AmTiO$_2$(+), respectively. The vertical axis "CHANGE IN ABSORBANCE" of FIG. 3 represents begins at the time of start of measurement and represents the percentage of decrease in absorbance due to pigment degradation, and an evaluation was made on the assumption that the percentage of change correlates positively with the amount of OH radicals generated. FIG. 3 shows that whereas there were slight increases in OH radicals in the case of US(+)AmTiO$_2$(−), where only ultrasonic irradiation was performed, and in the cases where a titanium oxide complex sheet was not irradiated with ultrasonic waves, there was a remarkable change in absorbance and therefore a remarkable increase in OH radicals in the case of US(+)AmTiO$_2$(+), where a titanium oxide complex sheet was irradiated with ultrasonic waves. Therefore, FIG. 3 shows that ultrasonic irradiation of a titanium oxide complex sheet generates OH radicals and thereby causes a surface of the titanium oxide complex sheet to exert bactericidal action and antibacterial action.

Further, the slopes of the curves of FIG. 3 show that the rate at which OH radicals are generated in the case of US(+)AmTiO$_2$(+) is highest immediately after the start of ultrasonic irradiation. This is considered to suggest that ultrasonic irradiation of a titanium oxide complex sheet exerts immediate bactericidal action and immediate antibacterial action. This shows that sufficient OH radicals can be generated even in cases where a comparatively low sound output safe to living organisms is used in exciting a titanium oxide complex sheet with ultrasonic waves.

Example 2

Methodology

For the purpose of checking the effect of stimulation of angiogenesis by ultrasonic irradiation of a titanium oxide complex sheet, the amounts of tumor necrosis factor (TNFα) produced in four patterns (namely (1) US(−)AmTiO$_2$(−), (2) US(+)AmTiO$_2$(−), (3) US(−)AmTiO$_2$(+), and (4) US(+)AmTiO$_2$(+)) of combinations of the presence or absence of ultrasonic irradiation (US) and the presence or absence of a titanium oxide complex sheet (AmTiO$_2$) were determined. It should be noted that TNFα is known as an indirect angiogenesis stimulator, produced from fat cells, macrophages, lymphocytes, etc., which induces vascular endothelial growth factor (refer to P. Reher et al.: *CYTOKINE*, 11, 416-423 (1999) and A. L. Harris: *Lancet*, 349 (suppl II), 13-15 (1997)). Furthermore, the numbers of cells that survived in the four patterns were evaluated simultaneously.

(Cell Culture)

Human bone marrow-derived mononuclear cells (Lot No. 070912B, Lonza Walkersville, Inc., Md., USA) were cultured in a medium RPMI 1640 (GIBCO) at 37° C. in the presence of 5% CO$_2$ with the medium having 10% fetal bovine serum and penicilin/streptomycine (GIBCO) added thereto.

(Ultrasonic Irradiation)

The experimental system, shown in FIG. 2, into which the ultrasonic probe had been incorporated was used to irradiate samples under optimal conditions, i.e., with continuous ultrasonic waves for 5 minutes at a frequency of 0.5 MHz with and an output of 114 mW/cm$^2$.

(Measurement of TNFα in Cell Culture Medium Supernatants)

In each cell culture tube, cells adjusted to $1 \times 10^6$ cells/mL were scattered on a sample sheet (having a diameter of 15 mm), and then cultured for 24 hours. After the culture, the sample sheet was irradiated with ultrasonic waves at 37° C. for 5 minutes by immersing the cell culture tube in the irradiation tank of the experimental system of FIG. 2. After that, the cell culture tube was withdrawn from the irradiation tank, and then the cells were further cultured for 2 hours in an incubator. After that, the cell culture medium was separated from the cell culture tube, and then the cell culture tube was subjected to centrifugation at 2000×g for 5 minutes, with the result that a supernatant was collected. With use of Tumor Necrosis Factor Alpha Human, Biotrak ELISA System (GE Healthcare UK), specimens were put into wells of a well plate together with biotinylated TNFα antibodies, and then incubated at room temperature for 2 hours. After three times of washing with wash fluid, 100 μL of HRP labeled streptoavidin were added into each well, and then further incubation was performed at room temperature for 30 minutes. After further washing with wash fluid, 100 μL of a liquid in which a luminous substrate had been dissolved were added, and then incubation was performed for 30 minutes in a dark field. Then, measurement of absorbance at 450 nm was performed. After that, the amount of TNFα in the cell culture medium supernatant was calculated from an analytical curve.

(Measurement of the Number of Cells That Survived)

After ultrasonic irradiation, cell counting Kit 8 (sankojunyaku, Tokyo, Japan) was put in each cell culture tube, and then staining was performed for 3 hours in an incubator at 37° C. in the presence of 5% CO$_2$. After that, measurement of absorbance at 450 nm was performed, whereby the number of cells that survived was measured, so as to examine the effect of ultrasonic irradiation on the cells.

<Results>

Figure 4:
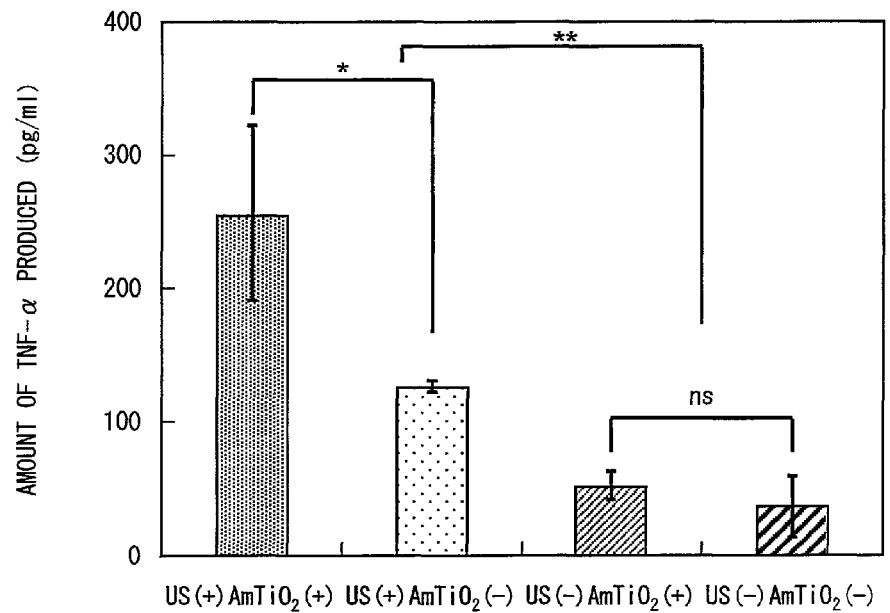
FIG. 4 is a graph, showing results of measuring the amounts of TNFα in cell supernatants in Example 2, on which "US(−)AmTiO$_2$(−)", "US(+)AmTiO$_2$(−)", "US(−)AmTiO$_2$(+)", and "US(+)AmTiO$_2$(+)" represent a result obtained by using an untreated silicon sheet and without ultrasonic irradiation, a result obtained by using an untreated silicon sheet and with ultrasonic irradiation, a result obtained by using a titanium oxide complex sheet and without ultrasonic irradiation, and a result obtained by using a titanium oxide complex sheet and with ultrasonic irradiation, respectively.

FIG. 4 shows results of the measurement of the amounts of TNFα in the cell culture medium supernatants. In FIG. 4, the mark "*" indicates a significant difference at a significance level of 5% according to a test of significance (n=4) of Student's t-test, and the mark "**" indicates a significant difference at a significance level of 1%. The mark "ns" indicates absence of a significant difference.

The results of FIG. 4 showed that ultrasonic irradiation significantly stimulates the production of TNFα from cells. It was further shown that the amount of TNFα produced from cells in the case where a titanium oxide complex sheet was irradiated with ultrasonic waves is significantly and remarkably higher than that in the case where an untreated silicone sheet was irradiated with ultrasonic waves. That is, it was confirmed that the production of TNFα from cells in contact with a titanium oxide complex sheet is significantly stimulated by irradiating the titanium oxide complex sheet with ultrasonic waves, whereby it was shown that an angiogenesis-stimulating effect is obtained in the vicinity of such cells.

Figure 5:
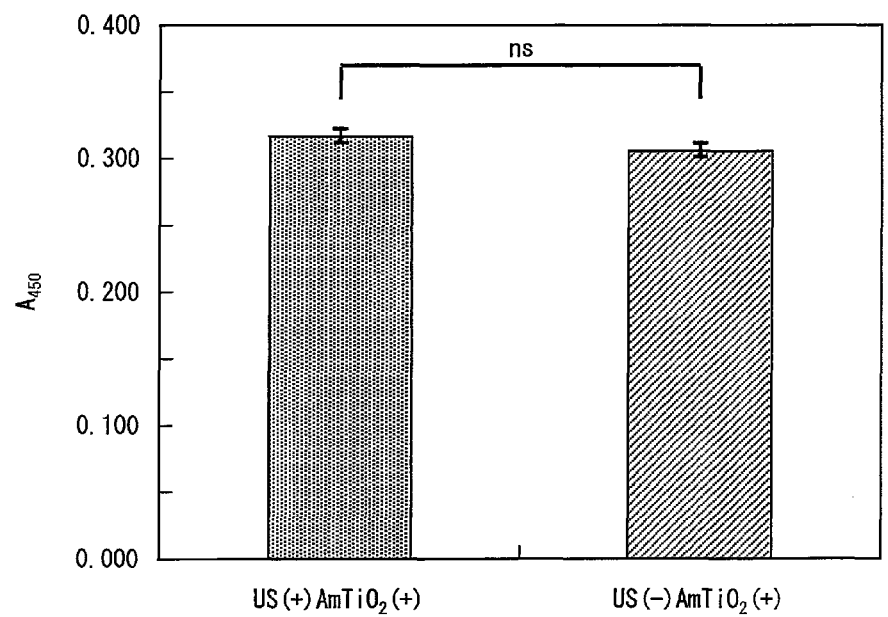
FIG. 5 is a graph, showing results of checking, in Example 2, the number of cells that survived in the case where ultrasonic irradiation was performed (US(+)AmTiO$_2$(+)) and the number of cells that survived in the case where no ultrasonic irradiation was performed (US(−)AmTiO$_2$(+)).

FIG. 5 shows results of checking, in Example 2, the number of cells that survived in the case where ultrasonic irradiation was performed (US(+)AmTiO$_2$(+)) and the number of cells that survived in the case where no ultrasonic irradiation was performed (US(−)AmTiO$_2$(+)). According to the results of FIG. 5, there was no significant difference between the number of cells that survived in the case where ultrasonic irradiation was performed (US(+)AmTiO$_2$(+)) and the number of cells that survived in the case where no ultrasonic irradiation was performed (US(−)AmTiO$_2$(+)). Therefore, it is judged that ultrasonic irradiation has no particular negative effect on cells. It should be noted that the mark "ns" of FIG. 5 has the same meaning as that of FIG. 4.

Example 3

Methodology (Cell Culture)

Human bone marrow-derived mononuclear cells (Lot No. 071853A, Lonza Walkersville, Inc., Md., USA) were cultured in a medium RPMI 1640 (GIBCO) with FBS (−) at 37° C. in the presence of 5% CO$_2$.

(Ultrasonic Irradiation)

The experimental system, shown in FIG. 2, into which the ultrasonic probe had been incorporated was used to irradiate samples with continuous ultrasonic waves for 5 minutes at a frequency of 493.8 kHz with an output of 225 mW/cm$^2$.

(Measurement of Vascular Endothelial Growth Factor (VEGF) in Cell Culture Medium Supernatants)

In each cell culture tube, a cell suspension prepared at 1×10$^6$ cells/mL was scattered on a sample sheet (i.e., a polyester (PET) sheet having a diameter of 15 mm), and then cultured for 24 hours. After the culture, the sample sheet was irradiated with ultrasonic waves at 37° C. for 5 minutes by immersing the cell culture tube in the irradiation tank of the experimental system of FIG. 2. After that, the cell culture tube was withdrawn from the irradiation tank, and then the cells were further cultured for 24 hours in an incubator. After that, the cell culture medium was separated from the cell culture tube, and then the cell culture tube was subjected to centrifugation at 2000×g for 5 minutes, with the result that a cell supernatant was collected. With use of Amersham Biotrak Vascular Endothelial Growth Factor, Human ELISA System (GE Healthcare UK), specimens were put into wells of a well plate together with diluting liquid, and then incubated at room temperature for 2 hours. After removal of reaction liquid from each well, washing was performed with washing fluid three times. After that, 100 μL of biotinylated VEGF second antibodies was put into each well, and then incubation was performed at room temperature for 1 hour. After three times of washing with wash fluid, 100 μL of HRP labeled streptoavidin were added into each well, and then further incubation was performed at room temperature for 30 minutes. After further washing with wash fluid, 100 μL of a liquid in which a luminous substrate had been dissolved were added, and then incubation was performed for 30 minutes in a dark field. Then, measurement of absorbance at 450 nm was performed. After that, the amount of VEGF in the cell culture medium supernatant was calculated from an analytical curve.

It should be noted that the sample sheet used in the present example is a titanium oxide complex sheet prepared by causing aminated titanium oxide particles to bind chemically with a PET sheet. The aminated titanium oxide, used for the production of the titanium oxide complex PET sheet, into which amino groups had been introduced was obtained by drying titanium oxide particles (particle diameter of 35 nm, anatase-type, specific surface of 9.66 m$^2$/g; manufactured by Ishihara Sangyo Kaisha Ltd.) at 120° C. for 24 hours, pouring 5.0 g of the titanium oxide particles, 100 ml of anhydrous toluene, and 0.5 ml of 3-aminopropyltrimethoxysilane (manufactured by Shin-Etsu Silicone Co., Ltd.; numbered KBM-903) into a three-necked flask having a capacity of 300 ml, and then refluxing the resultant mixture at 30° C. for 5 minutes. The aminated titanium oxide thus obtained was purified by spinning down with a large amount of toluene and then dried at 60° C. all day and night.

The PET sheet was put into an ozone water treatment apparatus (manufactured by Iwatani International Corporation) in 600 mg, and then subjected to the action of ozone water in an ozone concentration of 14 ppm for 20 minutes. The PET sheet thus treated with ozone water was transferred to a test tube. Then, 18 ml of distilled water, 35 mg of pentaethylene glycol dodecyl ether, which served as a nonionic surfactant, and 500 mg of methacryloxypropyltriethylsilane (manufactured by Shin-Etsu Chemical Co., Ltd., numbered KBE-503; hereinafter referred to as "KBE") were added into the test tube, and then mixed with the PET sheet. Next, after the interior of the test tube was repeatedly deaerated sufficiently and filled with nitrogen gas, and then the test tube was sealed. Then, the resultant mixture was allowed to react at 50° C. for 1 hour, with the result that a PET sheet (hereinafter referred to as "KBE-PET") was obtained in which a polymer chain having an alkoxysilyl group at a terminal thereof had been grafted.

Furthermore, aminated titanium oxide nanoparticles (amount introduced: 2 to 4 molecules/nm$^2$) obtained by introducing amino groups onto particle surfaces with a silane coupling agent were dispersed in ethanol with a ratio of 1 mg/ml, and the KBE-PET was immersed in the dispersion liquid. Then, the KBE-PET thus immersed was withdrawn and washed sufficiently with ethanol. After that, the KBE-PET was subjected to a coupling reaction at 80° C. for 2 hours. After the reaction, the resultant product was immersed in distilled water, treated by a probe-type ultrasonic generator for 3 minutes with an output of 20 kHz and 35 W, and then rid of unreacted aminated titanium oxide nanoparticles, with the result that the sample sheet used in the present example (titanium oxide complex sheet) was obtained.

<Results>

Figure 6:
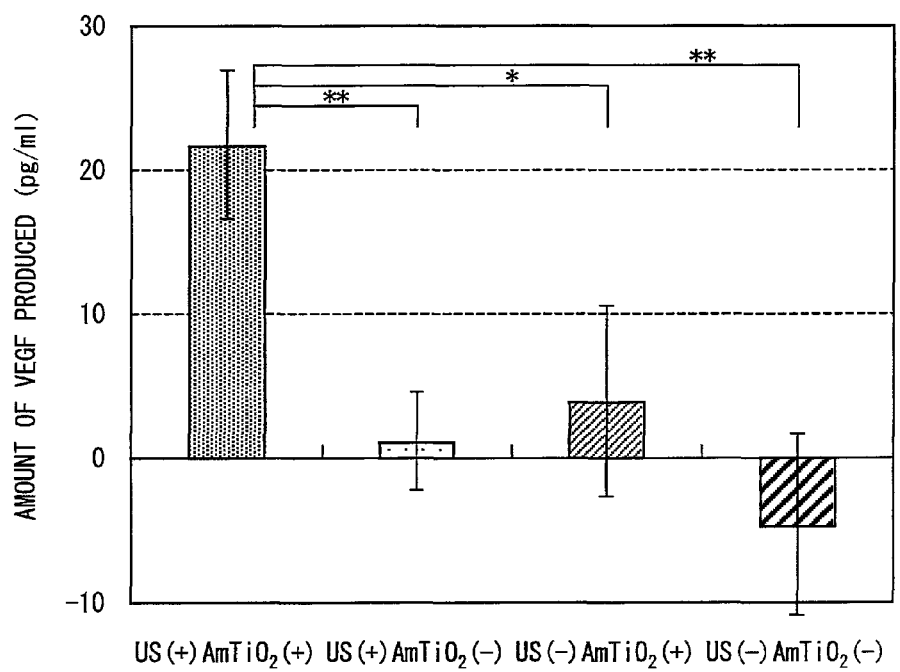
FIG. 6 is a graph, showing results of measuring the amounts of VEGF in cell supernatants in Example 3, on which "US(−)AmTiO$_2$(−)", "US(+)AmTiO$_2$(−)", "US(−)AmTiO$_2$(+)", and "US(+)AmTiO$_2$(+)" represent a result obtained by using an untreated polyester (PET) sheet and without ultrasonic irradiation, a result obtained by using an untreated polyester (PET) sheet and with ultrasonic irradiation, a result obtained by using a titanium oxide complex sheet and without ultrasonic irradiation, and a result obtained by using a titanium oxide complex sheet and with ultrasonic irradiation, respectively.

FIG. 6 shows results of the measurement of the amounts of VEGF in the cell culture medium supernatants. In FIG. 6, the mark "*" indicates a significant difference at a significance level of 5% according to a test of significance (n=3) of Student's t-test, and the mark "**" indicates a significant difference at a significance level of 1%.

The results of FIG. 6 showed that the amount of VEGF produced from cells in the case where a titanium oxide complex sheet was irradiated with ultrasonic waves was significantly and remarkably higher in comparison with the group of the result (represented by "US(−)AmTiO$_2$(+)" in FIG. 6) obtained by not irradiating a titanium oxide complex sheet with ultrasonic waves, the result (represented by "US(+)AmTiO$_2$(−)" in FIG. 6) obtained by irradiating an untreated PET sheet with ultrasonic waves, and the result (represented by "US(−)AmTiO$_2$(−)" in FIG. 6) obtained by not irradiating an untreated PET sheet with ultrasonic waves. That is, it was confirmed that the production of VEGF from cells that are in contact with a titanium oxide complex sheet is significantly stimulated by irradiating the titanium oxide complex sheet with ultrasonic waves, whereby it was shown that an angiogenesis-stimulating effect is obtained in the vicinity of such cells.

It should be noted that VEGF, which was measured as an index of angiogenesis in the present example, is known as a direct angiogenesis stimulator. Meanwhile, TNFα, which was measured as an index of angiogenesis in Example 2, is known as an indirect angiogenesis stimulator.

Further, whereas Example 2 used a silicone rubber sheet, the present example used a PET sheet. This is because a PET sheet takes the form of a fabric and, as such, has a wider surface area and a larger number of adherent cells than a film.

Example 4

Methodology (Animal Species)

A male Japanese white rabbit that weighed approximately 2.5 kg was devoted to an animal experiment.

(Implantation Test)

The rabbit was given a subcutaneous injection of 0.6 mL of Cercine (Takeda Chemical Industries, Ltd.) and 0.4 mL of Baytril (Bayer Yakuhin, Ltd.), and then fixed by a rabbit fixator. The rabbit was put under inhalation anesthesia on a respirator. After confirmation of anesthesia, the rabbit was defurred. His auricles were fixed with surgical tape, and then sterilized with ethanol for disinfection and 4% Hibiscrub (Dainippon Sumitomo Pharma Co., Ltd.; registered trademark). Furthermore, the operative fields were sterilized with Isodine (Meiji Seika Kaisha, Ltd.; registered trademark). Incisions about 5 mm long were made into his auricles with a Feather surgical blade No. 11 to form subcutaneous pockets. A sample (untreated polyester) 5 mm in diameter was implanted into the proximal side of each auricle, and a sample (titanium oxide complex sheet prepared by causing aminated titanium oxide particles to bind chemically with a PET sheet) was implanted into the distal side of each auricle. After confirmation of completion of implantation of the samples, each incision was sutured with a single stitch by using a 6.0 nylon yarn.

(Ultrasonic Irradiation Conditions)

The ultrasonic probe 21 of FIG. 1 was used to irradiate the sample-implanted sites with continuous ultrasonic waves for 1 minute at a frequency of 493.8 kHz with an output of 10 V (694 mW/cm$^2$) every day for 2 weeks after the date of sample implantation. Furthermore, the samples were irradiated under optimal conditions, i.e., with continuous ultrasonic waves for 5 minutes at a frequency of 500.0 kHz with an output of 5 V (81.3 mW/cm$^2$) every day for 2 weeks after 8 days of completion of the first irradiation.

(Evaluation Procedure)

The rabbit was sacrificed by intravenous administration of Somnopentyl (Kyoritsu Seiyaku Corporation). Specimens were obtained from the rabbit and fixed with 10% (w/v) formalin. Paraffin sections were prepared and evaluated by hematoxylin-eosin (HE) staining.

<Results>

FIG. 7 shows photographs (a) to (d) of specimens subjected to HE staining. The photograph (a) shows a result obtained by using a titanium oxide complex sheet and without ultrasonic irradiation (US(−)AmTiO$_2$(+)). The photograph (b) shows a result obtained by using a titanium oxide complex sheet and with ultrasonic irradiation (US(+)AmTiO$_2$(+)). The photograph (c) shows a result obtained by using an untreated polyester (PET) sheet and without ultrasonic irradiation (US(−)AmTiO$_2$(−)). The photograph (d) shows a specimen obtained by using an untreated polyester (PET) sheet and with ultrasonic irradiation (US(+)AmTiO$_2$(−)).

According to the results of FIG. 7, it is confirmed that solid angiogenesis had occurred in the tissue surrounding the titanium oxide complex sheet irradiated with ultrasonic waves (see the arrows in FIG. 7(b)). The result obtained by irradiating a titanium oxide complex sheet with ultrasonic waves showed a remarkably higher angiogenesis-stimulating effect in comparison with the group of the result obtained by not irradiating a titanium oxide complex sheet with ultrasonic waves (see FIG. 7(a)), the result obtained by irradiating an untreated PET sheet with ultrasonic waves (see FIG. 7(d)), and the result obtained by not irradiating an untreated PET sheet with ultrasonic waves (see FIG. 7(c)). That is, it was confirmed that ultrasonic irradiation of a titanium oxide complex sheet stimulates angiogenesis in tissue that is in contact with the titanium oxide complex sheet. It was also shown by the animal experiment that an angiogenesis-stimulating effect is obtained in the vicinity of such tissue.

The present invention irradiates, with ultrasonic waves, a titanium oxide material (titanium oxide alone or a titanium oxide composite material) existing on a surface of a medical device, thereby causing the surface of the medical device to exert beneficial effects such as antibiotic action, the stimulation of angiogenesis, and the degradation of a blood clot and a biofilm. Therefore, the present invention can be used across the fields of medicine and medical device industry.

The present invention is not limited to the description of the embodiments above, but may be altered by a skilled person within the scope of the claims. An embodiment based on a proper combination of technical means disclosed in different embodiments is encompassed in the technical scope of the present invention.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

What is claimed is:

1. A method of stimulating angiogenesis of a tissue in the vicinity of an implantable medical device by use of an ultrasonic medical apparatus including an ultrasonic irradiation means including a transducer, the method comprising the steps of:

implanting, into a body, the implantable medical device whose surface has been covered with a titanium oxide material; and extracorporeally irradiating, by use of the ultrasonic irradiation means including the transducer, with ultrasonic waves, the titanium oxide material provided on the surface of the implantable medical device thus implanted, the titanium oxide material being a titanium oxide composite material produced by covering a surface of a polymer base material with titanium oxide, the titanium oxide composite material being composed of
(a) a polymer base material having an active group and
(b) titanium oxide having a reactive functional group capable of reacting with the active group, and the titanium oxide composite material being produced through chemical bonding between the active group and the reactive functional group.

2. The method of stimulating angiogenesis as set forth in claim 1, wherein the irradiating by the ultrasonic irradiation means includes radiating ultrasonic waves with an output falling within safety standards for living organisms.

3. The method of stimulating angiogenesis as set forth in claim 1, further comprising adjusting the output of ultrasonic waves of the ultrasonic irradiation means.

4. The method of stimulating angiogenesis as set forth in claim 1, wherein the irradiating by the ultrasonic irradiation means includes generating one or more types of ultrasonic waves selected from the group consisting of continuous waves, pulse waves, burst waves, and standing waves.

5. The method of stimulating angiogenesis as set forth in claim 1, wherein the irradiating by the ultrasonic irradiation means includes radiating focused ultrasonic waves.

6. The method of stimulating angiogenesis as set forth in claim 1, wherein the ultrasonic irradiation means further includes a coupler.

7. The method of stimulating angiogenesis as set forth in claim 1,
wherein the transducer, which constitutes the ultrasonic irradiation means, is composed of a piezoelectric substance having a coefficient of electromechanical coupling of not less than 10%.

8. The method of stimulating angiogenesis as set forth in claim 7, wherein the transducer, which constitutes the ultrasonic irradiation means, is composed of a piezoelectric substance that is a quartz crystal, a water-soluble crystal, a piezo-ceramic, a polymer piezoelectric material, a highly-bound piezoelectric material, a composite piezoelectric material, an electrodeposited piezoelectric material, or any combination of the materials.

9. The method of stimulating angiogenesis as set forth in claim 1, wherein the irradiating by the ultrasonic irradiation means includes generating ultrasonic waves at a frequency of not less than 150 kHz.

10. The method of stimulating angiogenesis as set forth in claim 1, wherein the irradiating by the ultrasonic irradiation means includes generating, in a single transmission, ultrasonic waves containing higher harmonic waves or multi-frequency waves.

11. The method of stimulating angiogenesis as set forth in claim 1, wherein the reactive functional group is an amino group.

12. The method of stimulating angiogenesis as set forth in claim 1, wherein the reactive functional group is a hydroxyl group.

13. The method of stimulating angiogenesis as set forth in claim 1, wherein the titanium oxide composite material satisfies either or both of the following conditions (i) and (ii):
 (i) the titanium oxide composite material is composed of (a) the polymer base material having the active group and (b) the titanium oxide having the reactive functional group, wherein the reactive functional group is an amino group, and is produced through chemical bonding between the active group and the amino group; and
 (ii) the titanium oxide composite material is produced through chemical bonding between the reactive functional group possessed by titanium oxide, wherein the reactive functional group is a hydroxyl group, and the active group, possessed by a polymer base material, which is capable of forming the chemical bond with the hydroxyl group.

14. The method of stimulating angiogenesis as set forth in claim 1, wherein the medical device surface has been covered with the titanium oxide material by flocking.

\* \* \* \* \*